(12) United States Patent
Schudok et al.

(10) Patent No.: US 7,205,315 B2
(45) Date of Patent: Apr. 17, 2007

(54) BICYCLIC IMINO ACID DERIVATIVES AS INHIBITORS OF MATRIX METALLOPROTEINASES

(75) Inventors: Manfred Schudok, Eppstein/Ts. (DE); Hans Matter, Langenselbold (DE); Armin Hofmeister, Oppenheim (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 10/950,802

(22) Filed: Sep. 27, 2004

(65) Prior Publication Data

US 2005/0080127 A1    Apr. 14, 2005

Related U.S. Application Data

(60) Provisional application No. 60/542,081, filed on Feb. 5, 2004.

(30) Foreign Application Priority Data

Sep. 27, 2003    (DE) ................. 103 44 936

(51) Int. Cl.
A61K 31/4725    (2006.01)
C07D 217/22    (2006.01)
C07D 217/24    (2006.01)
(52) U.S. Cl. ............... 514/309; 546/141; 546/142
(58) Field of Classification Search ............ None
See application file for complete search history.

(56) References Cited

U.S. PATENT DOCUMENTS

| | | | |
|---|---|---|---|
| 4,691,022 A | 9/1987 | Henning et al. | |
| 4,902,695 A | 2/1990 | Ornstein et al. | |
| 5,430,023 A | 7/1995 | Gesellchen et al. | |
| 5,726,159 A | 3/1998 | Aaron et al. | |
| 5,990,145 A * | 11/1999 | Wehner et al. ............ | 514/388 |
| 6,207,672 B1 | 3/2001 | Thorwart | |
| 6,376,506 B1 * | 4/2002 | Brokàet al. ............... | 514/292 |
| 6,573,277 B2 | 6/2003 | Thorwart | |

FOREIGN PATENT DOCUMENTS

| EP | 0643073 | 3/1995 |
|---|---|---|
| EP | 0672665 | 9/1995 |
| WO | WO 94/28889 | 12/1994 |
| WO | WO 03/041641 | 5/2003 |

OTHER PUBLICATIONS

2002:312012 HCAPLUS.*
Fisher et al., "Recent Advances in MMP Inhibitor Design," Cancer Metastasis Review, vol. 25, pp. 115-136 (2006).*
Broka et al., STN International (2006), HCPLUS Database, Accession No.: 2002:312012., RN 210915-36-9.*
U.S. Appl. No. 10/376,287, filed Nov. 4, 1996, Thorwart.
Alcaide, et al., The Intramolecular Aldol Condensation Route to Fused Bi- and Tricyclic-B-Lactams1,2, J. Org. Chem. (1996) vol. 61 7125-7132.
Bergmeier, et al., Synthesis of Bicyclic Proline Analogs Using a Formal [3 +2] Intramolecular Aziridine-Allylsilane Cycloaddition Reaction, Tetrahedron vol. 55 (1999) pp. 8025-8038.
Creemers, E.J.M., et al., Matrix Metalloproteinase Inhibition after Myocardial Infarction A New Approach to Prevent Heart Failure?, Circulation Res. vol. 89, (2001) pp. 201-210.
Esch, et al., Reductive Cyclization of Carbon-Centered Glycine Radicals; A Novel Synthetic route to Cyclic a-Amino Acids, Tetrahedron vol. 48, No. 22, (1992) pp. 4659-4676.
George, S. et al., Therapeutic Potential of Matrix Metalloproteinase Inhibitors in Atherosclerosis, Expert Opinion on Investigational Drugs (2000) vol. 9 No. 5, pp. 993-1007.
Henning, et al., Diastereoselective Synthesis of Bicyclic Amino Acids Via Ring Contraction of a-Chlorolactams, Tetrahedron Letters, vol. 24, No. 48, (1983) pp. 5339-5342.
Li, et al., Matrix Metalloproteinases in the Progression of Heart Failure Potential Therapeutic Implications, Drugs vol. 61 No. 9 (2001) pp. 1239-1252.
Massova Irina et al., Matrix Metalloproteinases: Structures, Evolution, and Diversification, The FASEB Journal, 1998, vol. 12, pp. 1075-1095.
Michaelides Michael R et al., Recent Advances in Matrix Metalloproteinases Inhibitors Research, Current Pharmaceutical Design, 1999, vol. 5, pp. 787-819.
Skiles, et al., The Design, Structure, and Therapeutic Application of Matrix Metalloproteinase Inhibitors, Current Medicinal Chemistry vol. 8 (2001) pp. 425-474.
Tverezovsky, et al., Synthesis of (2S,3R,4S)-3.4-Methanoproline and Analogues by Cyclopropylidene Insertion, Tetrahedron vol. 53, No. 43 (1997) pp. 14773-14792.
Ye Qi-Zhuang et al., Purification and Characterization of the Human Stromelysin Catalytic Domain Expressed in *Escherichia coli*, Biochemistry, 1992, vol. 31, pp. 11231-11235.
Yip, Desmond et al., Matrix Metalloproteinase Inhibitors: Applications in Oncology, Investigational New Drugs, 1999, vol. 17, pp. 387-399.

* cited by examiner

*Primary Examiner*—Kamal A. Saeed
*Assistant Examiner*—Andrew B. Freistein
(74) *Attorney, Agent, or Firm*—Ronald G. Ort

(57) ABSTRACT

The present invention is directed to a compound of formula (I), or a stereoisomer or a mixture of stereoisomer thereof in any ratio, or its physiologically tolerable salt, which is useful as an inhibitor of matrix metalloproteinase. The present invention is also directed to a pharmaceutical preparation comprising a pharmaceutically effective amount of at least one compound of formula (I); processes for their preparation; the use of a compound of formula (I) having activity as an matrix metalloproteinase inhibitor; and for the prophylaxis and therapy of disease states that involve an increase in the activity of matrix metalloproteinase.

8 Claims, No Drawings

BICYCLIC IMINO ACID DERIVATIVES AS INHIBITORS OF MATRIX METALLOPROTEINASES

FIELD OF THE INVENTION

The present invention relates to novel derivatives of saturated bicyclic imino acids, such as, in particular, decahydroisoquinoline-1-carboxylic acid, to methods for preparing them, and to the use thereof as pharmaceuticals.

BACKGROUND OF THE INVENTION

In diseases such as osteoarthritis and rheumatism, destruction of the joint takes place, with this destruction being caused, in particular, by the proteolytic breakdown of collagen due to collagenases. Collagenases belong to the metalloproteinase (MP) or matrix metalloproteinase (MMP) superfamily. The MMPs form a group of Zn-dependent enzymes which are involved in the biological breakdown of the extracellular matrix (D. Yip et al. in Investigational New Drugs 17 (1999), 387–399 and Michaelides et al. in Current Pharmaceutical Design 5 (1999) 787–819). These MMPs are, in particular, able to break down fibrillar and nonfibrillar collagen and also proteoglycans, both of which are important matrix constituents. MMPs are involved in processes of wound healing, tumor invasion and metastasis migration, and also in angiogenesis, multiple sclerosis and heart failure (Michaelides, page 788; see above). In particular, they play an important role in the breakdown of the joint matrix in arthrosis and arthritis, whether this be osteoarthrosis, osteoarthritis or rheumatoid arthritis.

The activity of the MMPs is furthermore essential for many of the processes which play a role in atherosclerotic plaque formation, such as the infiltration of inflammatory cells and smooth muscle cell migration, as well as proliferation and angiogenesis (S. J. George, Exp. Opin. Invest. Drugs (2000), 9 (5), 993–1007). Furthermore, the degradation of matrix by MMPs can cause anything from plaque instabilities through to ruptures, with these conditions being able to give rise to the clinical symptoms of atherosclerosis, unstable angina pectoris, myocardial infarction or stroke (E. J. M. Creemers et al., Circulation Res. 89, 201–210 (2001)). All in all, the MMP family as a whole is able to break down all the components of the extracellular matrix of the blood vessels; in normal blood vessels, therefore, their activity is to a very great degree subject to regulatory mechanisms. The increase in MMP activity during plaque formation and plaque instability is caused by an increase in cytokine-stimulated and growth factor-stimulated gene transcription, an increase in zymogen activation and an imbalance in the MMP/TIMP (tissue inhibitors of metalloproteases) ratio. It therefore seems plausible that an MMP inhibition or the reattainment of the MMP-TIMP balance, would be helpful in treating atherosclerotic diseases. It is likewise becoming ever more clear that an increase in MMP activity is at least partially responsible for other cardiovascular diseases in addition to atherosclerosis, such as restenosis, dilated cardiomyopathy and the previously mentioned myocardial infarction. It has been shown that administering synthetic inhibitors to experimental animal models of these diseases is able to achieve marked improvements, for example in regard to the formation of atherosclerotic lesions, neointima formation, left ventricular remodeling, pump performance malfunction or infarction healing. In various preclinical studies using MMP inhibitors, detailed tissue analyses indicated a reduction in collagen damage, an improvement in extracellular matrix remodeling and an improvement in the structure and function of cardiac muscle and blood vessels. Among these processes, matrix remodeling processes and MMP-regulated fibroses, in particular, are regarded as being important components in the progression of heart diseases (infarction) (Drugs 61, 1239–1252 (2001)).

Under physiological conditions, MMPs cleave matrix proteins such as collagen, laminin, proteoglycans, elastin or gelatine, and also process (i.e. activate or inactivate), by means of cleavage, a large number of other proteins and enzymes, which means that they play an important role in the entire body, with this role being particularly significant in the connective tissue and bones.

A large number of different MMP inhibitors are known (EP 0 606 046; WO 94/28889; WO 96/27583; cf. reviews such as Current Medicinal Chemistry 8, 425–74 (2001) as well). Following the first clinical studies in humans, it has now been found that MMPs give rise to side-effects. The side-effects to be mentioned are musculoskeletal pain or anthralgias. The prior art makes it clear that it is expected that more selective inhibitors would be able to reduce these side-effects (Yip, page 387, see above). Specificity towards MMP-1 is particularly to be emphasized in this connection since these unwanted side-effects evidently appear to an increased extent when MMP-1 is inhibited.

A disadvantage of the known MMP inhibitors is therefore that they frequently lack specificity. Most MMP inhibitors inhibit many MMPs simultaneously because the catalytic domains of the MMPs possess similar structures. As a consequence, the inhibitors also undesirably affect the enzymes which have a vital function (Massova I, et al., The FASEB Journal (1998) 12, 1075–1095).

In the endeavor to find effective compounds for treating connective tissue diseases, it has now been found that the derivatives which are employed in accordance with the invention are powerful inhibitors of the matrix metalloproteinases MMP-2, MMP-3, MMP-8, MMP-9 and MMP-13 while only having a weak inhibitory effect on MMP-1.

SUMMARY OF THE INVENTION

The invention therefore relates to a compound of the formula I

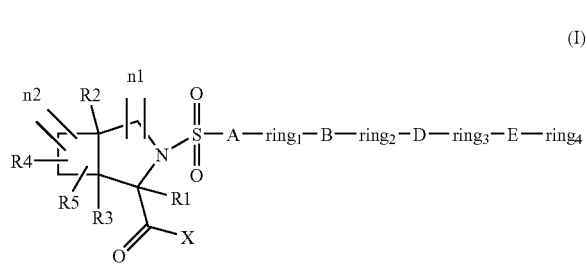

and/or to all the stereoisomeric forms of the compound of the formula I and/or to mixtures of these forms in any ratio, and/or to a physiologically tolerated salt of the compound of the formula I, wherein A is —($C_0$–$C_4$)-alkylene, B, D and E are identical or different and are, independently of each other, —($C_0$–$C_4$)-alkylene or the radical -B1-B2-B3- in which B1 is —$(CH_2)_n$—, in which n is the integer zero, 1 or 2, B3 is —$(CH_2)_m$—, in which m is the integer zero, 1 or 2, with the proviso that the sum of n and m amounts to zero, 1 or 2, and B2 is
1) —C(O)—
2) —(C$_2$–C$_4$)-alkenylene,
3) —S(O)$_o$—, where o is the integers zero, 1 or 2,
4) —N(R6)-, in which R6 is hydrogen atom, methyl or ethyl,
5) —N(R6)-C(Y)—, in which Y is oxygen atom or sulfur atom and R6 is defined as above,
6) —C(Y)—N(R6)-, in which Y is oxygen atom or sulfur atom and R6 is defined as above,
7) —N(R6)-SO$_2$—, in which R6 is defined as above,
8) —SO$_2$—N(R6)-, in which R6 is defined as above,
9) —N(R6)-SO$_2$—N(R6)-, in which R6 is defined as above,
10) —N(R6)-C(Y)—N(R6)-, in which Y is oxygen atom or sulfur atom and R6 is defined as above,
11) —O—C(O)—N(R6)-,
12) —NH—C(O)—O—,
13) —O—,
14) —C(O)—O—,
15) —O—C(O)—,
16) —O—C(O)—O—,
17) —O—CH$_2$—C(O)—,
18) —O—CH$_2$—C(O)—O—,
19) —O—CH$_2$—C(O)—N(R6)-, in which R6 is defined as above,
20) —C(O)—CH$_2$—O—,
21) —O—C(O)—CH$_2$—O—,
22) —N(R6)-C(O)—CH$_2$—O—, in which R6 is defined as above,
23) —O—(CH$_2$)$_n$—O—, in which n is the integer 2 or 3, or
24) —O—(CH$_2$)$_m$—N(R6)-, in which m is the integer 2 or 3 and R6 is defined as above,
25) —N(R6)-(CH$_2$)$_m$—O—, in which m is the integer 2 or 3 and R6 is defined as above,
26) —N(R6)-N(R6)-, in which R6 is defined as above,
27) —N=N—,
28) —N(R6)-CH=N—, in which R6 is defined as above,
29) —N=CH—N(R6)-, in which R6 is defined as above,
30) —N(R6)-C(R7)=N—, in which R6 is defined as above and R7 is —NH—R6,
31) —N=C(R7)-N(R6)-, in which R6 is defined as above and R7 is —NH—R6, or
32) —(C$_2$–C$_6$)-alkynylene, ring 1, ring 2 and ring 3 are identical or different and are, independently of each other,
1) covalent bond,
2) —(C$_6$–C$_{14}$)-aryl, in which aryl is unsubstituted or substituted, independently of each other, once, twice or three times, by G, or
3) 4- to 15-membered Het ring, in which Het ring is unsubstituted or substituted, independently of each other, once, twice or three times, by G, ring 4 is
1) —(C$_6$–C$_{14}$)-aryl, in which aryl is unsubstituted or substituted, independently of each other, once, twice or three times, by G,
2) 4- to 15-membered Het ring, in which the Het ring is unsubstituted or substituted, independently of each other, once, twice or three times, by G, or 3) is one of the following radicals

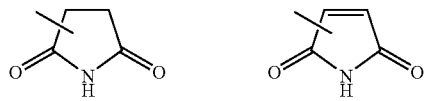

and these radicals are unsubstituted or substituted once by G,

G is 1) hydrogen atom,
2) halogen,
3) =O,
4) —(C$_1$–C$_6$)-alkyl, in which alkyl is unsubstituted or substituted, once, twice or three times, by halogen, —(C$_3$–C$_6$)-cycloalkyl, —(C$_2$–C$_6$)-alkynyl, —(C$_6$–C$_{14}$)-aryl or Het ring,
5) —(C$_6$–C$_{14}$)-aryl,
6) Het ring,
7) —C(O)—O—R10, in which R10 is
   a) —(C$_1$–C$_6$)-alkyl, in which alkyl is unsubstituted or substituted, once or twice, by —(C$_3$–C$_6$)-cycloalkyl, —(C$_2$–C$_6$)-alkynyl, —(C$_6$–C$_{14}$)-aryl or Het ring, or
   b) —(C$_6$–C$_{14}$)-aryl or Het ring,
8) —C(S)—O—R10, in which R10 is defined as above,
9) —C(O)—NH—R11, in which R11 is
   a) —(C$_1$–C$_6$)-alkyl, in which alkyl is unsubstituted or substituted, once or twice, by —(C$_3$–C$_6$)-cycloalkyl, —(C$_6$–C$_{14}$)-aryl or Het ring, or
   b) —(C$_6$–C$_{14}$)-aryl or Het ring,
10) —C(S)—NH—R11, in which R11 is defined as above,
11) —O—R12, in which R12 is
   a) hydrogen atom,
   b) —(C$_1$–C$_6$)-alkyl, in which alkyl is unsubstituted or substituted, once, twice or three times, by halogen, —(C$_3$–C$_6$)-cycloalkyl, —(C$_2$–C$_6$)-alkynyl, —(C$_6$–C$_{14}$)-aryl or Het ring,
   c) —(C$_6$–C$_{14}$)-aryl,
   d) Het ring,
   e) —C(O)—O—R13, in which R13 is
      e)1) —(C$_1$–C$_6$)-alkyl, in which alkyl is unsubstituted or substituted, once or twice, by —(C$_3$–C$_6$)-cycloalkyl, —(C$_2$–C$_6$)-alkynyl, —(C$_6$–C$_{14}$)-aryl, or Het ring, or
      e)2) —(C$_6$–C$_{14}$)-aryl or Het ring,
   f) —C(S)—O—R13, in which R13 is defined as above,
   g) —C(O)—NH—R14, in which R14 is
      g)1) —(C$_1$–C$_6$)-alkyl, in which alkyl is unsubstituted or substituted, once or twice, by —(C$_3$–C$_6$)-cycloalkyl, —(C$_2$–C$_6$)-alkynyl, —(C$_6$–C$_{14}$)-aryl or Het ring, or
      g)2) —(C$_6$–C$_{14}$)-aryl or Het ring, or
   h) —C(S)—NH—R14, in which R14 is defined as above,
12) —C(O)—R10, in which R10 is defined as above,
13) —S(O)$_p$—R12, in which R12 is defined as above and p is the integers zero, 1 or 2,
14) —NO$_2$,
15) —CN, or
16) —N(R15)-R12, in which R15 is
   16)1) hydrogen atom,
   16)2) —(C$_1$–C$_6$)-alkyl, or
   16)3) —SO$_2$—(C$_1$–C$_6$)-alkyl, in which alkyl is unsubstituted or substituted, once or twice, by —(C$_3$–C$_6$)-cycloalkyl, —(C$_2$–C$_6$)-alkynyl, —(C$_6$–C$_{14}$)-aryl or Het ring, and R12 is defined as above, or 17) —SO$_2$—N(R12)-R1, in which R12 is defined as above and R1 is defined as below, X is —OH or —NH—OH, n1 is the integer 1, 2 or 3, n2 is the integer zero, 1, 2, 3 or 4, with the proviso that the sum of n1 and n2 amounts to 1, 2, 3, 4, 5, 6 or 7, R1, R2, R3, R4 and R5 are identical or different and are, independently of each other,
1) hydrogen atom,
2) —(C$_1$–C$_6$)-alkyl, in which alkyl is unsubstituted or substituted, once or twice, by —(C$_3$–C$_6$)-Cycloalkyl, —(C$_2$–C$_6$)-alkynyl, —(C$_6$–C$_{14}$)-aryl or Het ring,
3) —C(O)—O—R8, in which R8 is
   3)1) hydrogen atom,
   3)2) —(C$_1$–C$_6$)-alkyl, in which alkyl is unsubstituted or substituted, once or twice, by —(C$_3$–C$_6$)-cycloalkyl, —(C$_2$–C$_6$)-alkynyl, —(C$_6$–C$_{14}$)-aryl or Het ring, or substituted once to five times, by fluorine, or
   3)3) —(C$_6$–C$_{14}$)-aryl or Het ring,
4) —O—R8, in which R8 has the abovementioned meaning, or
5) —(C$_3$–C$_6$)-Cycloalkyl.

The invention also relates to the compound of the formula I where

A is —(C$_0$–C$_4$)-alkylene,

B, D and E are identical or different and are, independently of each other, —(C$_0$–C$_4$)-alkylene or the radical —B1-B2-B3- in which B1 is —(CH$_2$)$_n$—, in which n is the integer zero, 1 or 2, B3 is —(CH$_2$)$_m$—, in which m is the integer zero, 1 or 2, with the proviso that the sum of n and m amounts to zero, 1 or 2, and B2 is
1) —C(O)—
2) —(C$_2$–C$_4$)-alkenylene,
3) —S(O)$_o$—, where o is the integers zero, 1 or 2,
4) —N(R6)-, in which R6 is hydrogen atom, methyl or ethyl,
5) —N(R6)-C(Y)—, in which Y is oxygen atom or sulfur atom and R6 is defined as above,
6) —C(Y)—N(R6)-, in which Y is oxygen atom or sulfur atom and R6 is defined as above,
7) —N(R6)-SO$_2$—, in which R6 is defined as above,
8) —SO$_2$—N(R6)-, in which R6 is defined as above,
9) —N(R6)-SO$_2$—N(R6)-, in which R6 is defined as above,
10) —N(R6)-C(Y)—N(R6)-, in which Y is oxygen atom or sulfur atom and R6 is defined as above,
11) —O—C(O)—N(R6)-,
12) —NH—C(O)—O—,
13) —O—,
14) —C(O)—O—,
15) —O—C(O)—,
16) —O—C(O)—O—,
17) —O—CH$_2$—C(O)—,
18) —O—CH$_2$—C(O)—O—,
19) —O—CH$_2$—C(O)—N(R6)-, in which R6 is defined as above,
20) —C(O)—CH$_2$—O—,
21) —O—C(O)—CH$_2$—O—,
22) —N(R6)-C(O)—CH$_2$—O—, in which R6 is defined as above,
23) —O—(CH$_2$)$_n$—O—, in which n is the integer 2 or 3, or
24) —O—(CH$_2$)$_m$—N(R6)-, in which m is the integer 2 or 3 and R6 is defined as above,
25) —N(R6)-(CH$_2$)$_m$—O—, in which m is the integer 2 or 3 and R6 is defined as above,
26) —N(R6)-N(R6)-, in which R6 is defined as above,
27) —N═N—,
28) —N(R6)-CH═N—, in which R6 is defined as above,
29) —N═CH—N(R6)-, in which R6 is defined as above,
30) —N(R6)-C(R7)═N—, in which R6 is defined as above and R7 is —NH—R6,
31) —N═C(R7)-N(R6)-, in which R6 is defined as above and R7 is —NH—R6, or
32) —(C$_2$–C$_6$)-alkynylene, ring 1, ring 2 and ring 3 are identical or different and are, independently of each other,
1) covalent bond,
2) phenyl or naphthyl and are unsubstituted or substituted, independently of each other, once, twice or three times, by G, or
3) 4- to 15-membered Het ring, in which the Het ring is a radical from the series acridinyl, azepinyl, azetidinyl, aziridinyl, benzimidazalinyl, benzimidazolyl, benzofuranyl, benzothiofuranyl, benzothiophenyl, benzoxazolyl, benzothiazolyl, benzotriazolyl, benzotetrazolyl, benzisoxazolyl, benzisothiazolyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, deca-hydroquinolinyl, dibenzofuranyl, dibenzothiophenyl, dihydrofuran[2,3-b]tetrahydrofuranyl, dihydrofuranyl, dioxolyl, dioxanyl, 2H,6H-1,5,2-dithiazinyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl(benzimidazolyl), isothiazolidinyl, 2-isothiazolinyl, isothiazolyl, isoxazolyl, isoxazolidinyl, 2-isoxazolinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxothiolanyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyroazolidinyl, pyrazolinyl, pyrazolyl, pyridazinyl, pyridooxazolyl, pyridoimidazolyl, pyridothiazolyl, pyridothiophenyl, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrahydropyridinyl, 6H-1,2,5-thiadazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiomorpholinyl, thiophenyl, triazinyl, 1,2,3-triazolyl, 1,2,3-triazolyl, 1,2,4-triazolyl, 1,2,5-triazolyl, 1,3,4-triazolyl and xanthenyl, and these radicals are unsubstituted or substituted, independently of each other, once, twice or three times, by G, ring 4 is
1) —(C$_6$–C$_{14}$)-aryl, in which aryl is a radical from the series phenyl, naphthyl, 1-naphthyl, 2-naphthyl, anthryl and fluorenyl, and these radicals are unsubstituted or substituted, independently of each other, once, twice or three times, by G,
2) 4- to 15-membered Het ring, in which the Het ring is a radical from the series acridinyl, azepinyl, azetidinyl, aziridinyl, benzimidazalinyl, benzimidazolyl, benzofuranyl, benzothiofuranyl, benzothiophenyl, benzoxazolyl, benzothiazolyl, benzotriazolyl, benzotetrazolyl, benzisoxazolyl, benzisothiazolyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, deca-hydroquinolinyl, dibenzofuranyl, dibenzothiophenyl, dihydrofuran[2,3-b]tetrahydrofuranyl, dihydrofuranyl, dioxolyl, dioxanyl, 2H,6H-1,5,2-dithiazinyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolidinyl, 2-isothiazolinyl, isothiazolyl, isoxazolyl, isoxazolidinyl, 2-isoxazolinyl, 2'-methylbiphenyl-2-ol, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxothiolanyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyroazolidinyl, pyrazolinyl, pyrazolyl, pyridazinyl, pyridooxazolyl, pyridoimidazolyl, pyridothiazolyl, pyridothiophenyl, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrahydropyridinyl, 6H-1,2,5-thiadazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiomorpholinyl, thiophenyl, triazinyl, 1,2,3-triazolyl, 1,2,3-triazolyl, 1,2,4-triazolyl, 1,2,5-triazolyl, 1,3,4-triazolyl and xanthenyl, and are unsubstituted or substituted, independently of each other, once, twice or three times, by G, or 3) is one of the following radicals

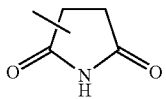 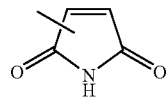

and these radicals are unsubstituted or substituted once by G,

G is 1) hydrogen atom,
2) halogen,
3) =O,
4) —($C_1$–$C_6$)-alkyl, in which alkyl is unsubstituted or substituted, once, twice or three times, by halogen, —($C_3$–$C_6$)-Cycloalkyl, —($C_2$–$C_6$)-alkynyl, —($C_6$–$C_{14}$)-aryl or Het ring, where aryl and Het ring are defined as above,
5) —($C_6$–$C_{14}$)-aryl, where aryl is defined as above,
6) Het ring, where Het ring is defined as above,
7) —C(O)—O—R10, in which R10 is
  a) —($C_1$–$C_6$)-alkyl, in which alkyl is unsubstituted or substituted, once or twice, by —($C_3$–$C_6$)-cycloalkyl, —($C_2$–$C_6$)-alkynyl, —($C_6$–$C_{14}$)-aryl or Het ring, where aryl and Het ring are defined as above, or
  b) —($C_6$–$C_{14}$)-aryl or Het ring, where aryl and Het ring are defined as above,
8) —C(S)—O—R10, where R10 is defined as above,
9) —C(O)—NH—R11, in which R11 is
  a) —($C_1$–$C_6$)-alkyl, in which alkyl is unsubstituted or substituted, once or twice, by —($C_3$–$C_6$)-cycloalkyl, —($C_2$–$C_6$)-alkynyl, —($C_6$–$C_{14}$)-aryl or Het ring, where aryl and Het ring are defined as above, or
  b) —($C_6$–$C_{14}$)-aryl or Het ring, where aryl and Het ring are defined as above,
10) —C(S)—NH—R11, in which R11 is defined as above,
11) —O—R12, in which R12 is
  a) hydrogen atom,
  b) —($C_1$–$C_6$)-alkyl, in which alkyl is unsubstituted or substituted, once, twice or three times, by halogen, —($C_3$–$C_6$)-cycloalkyl, —($C_2$–$C_6$)-alkynyl, —($C_6$–$C_{14}$)-aryl or Het ring, where aryl and Het ring are defined as above,
  c) —($C_6$–$C_{14}$)-aryl, where aryl is defined as above,
  d) Het ring, where Het ring is defined as above,
  e) —C(O)—O—R13, in which R13 is
    e)1) —($C_1$–$C_6$)-alkyl, in which alkyl is unsubstituted or substituted, once or twice, by —($C_3$–$C_6$)-cycloalkyl, —($C_2$–$C_6$)-alkynyl, —($C_6$–$C_{14}$)-aryl, or Het ring, where aryl and Het ring are defined as above, or
    e)2) —($C_6$–$C_{14}$)-aryl or Het ring, where aryl and Het ring are defined as above,
  f) —C(S)—O—R13, in which R13 is defined as above,
  g) —C(O)—NH—R14, in which R14 is
    g)1) —($C_1$–$C_6$)-alkyl, in which alkyl is unsubstituted or substituted, once or twice, by —($C_3$–$C_6$)-cycloalkyl, —($C_2$–$C_6$)-alkynyl, —($C_6$–$C_{14}$)-aryl or Het ring, where aryl and Het ring are defined as above, or
    g)2) —($C_6$–$C_{14}$)-aryl or Het ring, where aryl and Het ring are defined as above, or
  h) —C(S)—NH—R14, in which R14 is defined as above,
12) —C(O)—R10, in which R10 is defined as above,
13) —S(O)$_p$—R12, in which R12 is defined as above and p is the integers zero, 1 or 2,
14) —$NO_2$,
15) —CN, or
16) —N(R15)-R12, in which R15 is
  16)1) hydrogen atom, or
  16)2) —($C_1$–$C_6$)-alkyl and R12 is defined as above,
  16)3) —$SO_2$—($C_1$–$C_6$)-alkyl, in which alkyl is unsubstituted or substituted, once or twice, by —($C_3$–$C_6$)-cycloalkyl, —($C_2$–$C_6$)-alkynyl, —($C_6$–$C_{14}$)-aryl or Het ring,
17) —$SO_2$—N(R12)-R1, in which R12 is defined as above and R1 is defined as below, X is —OH or —NH—OH,
n1 is the integer 1 or 2,
n2 is the integer 2 or 3,
R1, R2, R3, R4 and R5 are identical or different and are, independently of each other,
1) hydrogen atom,
2) —($C_1$–$C_6$)-alkyl, in which alkyl is unsubstituted or substituted, once or twice, by —($C_3$–$C_6$)-Cycloalkyl, —($C_2$–$C_6$)-alkynyl, —($C_6$–$C_{14}$)-aryl or Het ring,
3) —C(O)—O—R8, in which R8 is
  3)1) hydrogen atom,
  3)2) —($C_1$–$C_6$)-alkyl, in which alkyl is unsubstituted or substituted, once or twice, by —($C_3$–$C_6$)-Cycloalkyl, —($C_2$–$C_6$)-alkynyl, —($C_6$–$C_{14}$)-aryl or Het ring, or is substituted once to five times by fluorine, or
  3)3) —($C_6$–$C_{14}$)-aryl or Het ring,
4) —O—R8, in which R8 has the above mentioned meaning, or
5) —($C_3$–$C_6$)-cycloalkyl.

The invention furthermore relates to the compound of the formula I wherein

A is —($C_0$–$C_4$)-alkylene,
B, D and E are identical or different and are, independently of each other, —($C_0$–$C_4$)-alkylene or the radical —B1-B2-B3- in which
B1 is —$(CH_2)_n$—, in which n is the integer zero, 1 or 2,
B3 is —$(CH_2)_m$—, in which m is the integer zero, 1 or 2, with the proviso that the sum of n and m amounts to zero, 1 or 2, and
B2 is
  1) —($C_0$–$C_2$)-alkylene,
  2) ethenylene,
  3) ethynylene,
  4) —C(O)—
  5) —N(R6)-C(O)—, in which R6 is hydrogen atom, methyl or ethyl,
  6) —C(O)—N(R6)-, in which R6 is defined as above,
  7) —O—, or
  8) —S—,
ring 1, ring 2 and ring 3 are identical or different and are, independently of each other,
  1) covalent bond,
  2) phenyl or naphthyl and are unsubstituted or substituted, independently of each other, once or twice, by G, or
  3) Het ring, in which the Het ring is a radical from the series dihydrofuranyl, furanyl, pyridinyl, pyrimidinyl, pyrrolyl, thiadiazolyl, thiazolyl or thiophenyl, and the radicals are unsubstituted or substituted, independently of each other, once or twice, by G,
ring 4 is
  1) phenyl or naphthyl and is unsubstituted or substituted, independently of each other, once or twice, by G,
  2) Het ring, in which the Het ring is a radical from the series benzofuranyl, dihydrofuranyl, dibenzofuranyl, dibenzothiophenyl, furanyl, 2'-methylbiphenyl-2-ol, morpholinyl, piperazinyl, piperidinyl, pyridinyl, pyrimidinyl, pyridothiophenyl, pyrrolyl, pyrrolidinyl, thiazolyl or thiophenyl and is unsubstituted or substituted, independently of each other, once or twice, by G, or
  3) the following radical

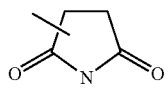

and this radical is unsubstituted or substituted once by G,
G is 1) hydrogen atom,
  2) Br, Cl or F,
  3) —($C_1$–$C_4$)-alkyl, in which alkyl is unsubstituted or substituted once or twice by F, phenyl, —$C_3$-cycloalkyl or Het ring, where Het ring is defined as above,
  4) phenyl,
  5) Het ring, where Het ring is defined as above,
  6) —C(O)—O—R10, in which R10 is
    a) —($C_1$–$C_6$)-alkyl, in which alkyl is unsubstituted or substituted, once or twice, by cyclopropyl, phenyl or Het ring, where Het ring is defined as above,
    b) phenyl, or
    c) Het ring, where Het ring is defined as above,
  7) —C(O)—NH—R11, in which R11 is
    a) —($C_1$–$C_6$)-alkyl, in which alkyl is unsubstituted or substituted, once or twice, by cyclopropyl, phenyl or Het ring, where Het ring is defined as above,
    b) phenyl, or
    c) Het ring, where Het ring is defined as above,
  8) —O—R12, in which R12 is
    a) hydrogen atom,
    b) —($C_1$–$C_6$)-alkyl, in which alkyl is unsubstituted or substituted, once, twice or three times, by halogen, cyclopropyl, phenyl or Het ring, where Het ring is defined as above,
    c) phenyl,
    d) Het ring, where Het ring is defined as above,
    e) —C(O)—O—R13, in which R13 is
      e)1) —($C_1$–$C_6$)-alkyl, in which alkyl is unsubstituted or substituted, once or twice, by cyclopropyl, phenyl or Het ring, where Het ring is defined as above, or
      e)2) phenyl or Het ring, where Het ring is defined as above,
    f) —C(S)—O—R13, in which R13 is defined as above, or
    g) —C(O)—NH—R14, in which R14 is
      g)1) —($C_1$–$C_6$)-alkyl, in which alkyl is unsubstituted or substituted, once or twice, by phenyl or Het ring, where Het ring is defined as above, or
      g)2) phenyl or Het ring, where Het ring is defined as above,
  9) —C(O)—R10, in which R10 is defined as above,
  10) —$S(O)_p$—R12, in which R12 is defined as above and p is the integers 1 or 2,
  11) —$NO_2$,
  12) —CN, or
  13) —N(R15)-R12, in which R15 is
    13)1) hydrogen atom, or
    13)2) —($C_1$–$C_6$)-alkyl and R12 is defined as above,
X is —OH or —NH—OH,
n1 is the integer 1 or 2,
n2 is the integer 2 or 3,
R1, R2 and R3 are in each case hydrogen atom,
R4 and R5 are identical or different and are, independently of each other,
  1) hydrogen atom,
  2) methyl,
  3) ethyl, or
  4) —OH.

The invention furthermore relates to the compound of the formula I wherein
A is —($C_0$–$C_4$)-alkylene,
B, D and E are identical or different and are, independently of each other, —($C_0$–$C_4$)-alkylene or the radical —B1-B2-B3- in which
B1 is —$(CH_2)_n$—, in which n is the integer zero, 1 or 2,
B3 is —$(CH_2)_m$—, in which m is the integer zero, 1 or 2, with the proviso that the sum of n and m amounts to zero, 1 or 2, and
B2 is
  1) —($C_0$–$C_2$)-alkylene,
  2) ethenylene, or
  3) ethynylene,
ring 1, ring 2 and ring 3 are identical or different and are, independently of each other,
  1) covalent bond,
  2) phenyl, and are unsubstituted or substituted, independently of each other, once or twice, by G, or
  3) Het ring, in which the Het ring is a radical from the series dihydrofuranyl, furanyl, morpholinyl, piperazinyl, piperidinyl, pyridinyl, pyrimidinyl, pyrrolyl, thiazolyl or thiophenyl, and are unsubstituted or substituted, independently of each other, once or twice, by G, ring 4 is
1) phenyl, and is unsubstituted or substituted, independently of each other, once or twice, by G,
2) Het ring, in which the Het ring is a radical from the series benzofuranyl, dihydrofuranyl, dibenzofuranyl, dibenzothiophenyl, furanyl, 2'-methylbiphenyl-2-ol, morpholinyl, piperazinyl, piperidinyl, pyridinyl, pyrimidinyl, pyridothiophenyl, pyrrolyl, pyrrolidinyl, thiazolyl or thiophenyl and is unsubstituted or substituted, independently of each other, once or twice, by G, or
3) the following radical

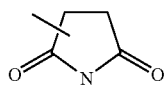

and this radical is unsubstituted or substituted once by G,
G is 1) hydrogen atom,
2) Br, Cl or F,
3) —($C_1$–$C_4$)-alkyl, in which alkyl is unsubstituted or substituted once, twice or three times, by Br, Cl, F, —$C_3$-Cycloalkyl, phenyl or Het ring, where Het ring is defined as above,
4) phenyl,
5) Het ring, where Het ring is defined as above,
6) —C(O)—O—R10, in which R10 is
  a) —($C_1$–$C_6$)-alkyl, in which alkyl is unsubstituted or substituted, once or twice, by cyclopropyl, phenyl or Het ring, where Het ring is defined as above,
  b) phenyl, or
  c) Het ring, where Het ring is defined as above,
7) —C(O)—NH—R11, in which R11 is
  a) —($C_1$–$C_6$)-alkyl, in which alkyl is unsubstituted or substituted, once or twice, by cyclopropyl, phenyl or Het ring, where Het ring is defined as above,
  b) phenyl or naphthyl, or
  c) Het ring, where Het ring is defined as above,
8) —O—R12, in which R12 is
  a) hydrogen atom,
  b) —($C_1$–$C_6$)-alkyl, in which alkyl is unsubstituted or substituted, once, twice or three times, by halogen, cyclopropyl, phenyl or Het ring, where Het ring is defined as above,
  c) phenyl,
  d) Het ring, where Het ring is defined as above,
  e) —C(O)—O—R13, in which R13 is
    e)1) —($C_1$–$C_6$)-alkyl, in which alkyl is unsubstituted or substituted, once or twice, by cyclopropyl, phenyl, naphthyl, or Het ring, where Het ring is defined as above, or
    e)2) phenyl or Het ring, where Het ring is defined as above,
  f) —C(S)—O—R13, in which R13 is defined as above, or
  g) —C(O)—NH—R14, in which R14 is
    g)1) —($C_1$–$C_6$)-alkyl, in which alkyl is unsubstituted or substituted, once or twice, by phenyl or Het ring, where Het ring is defined as above, or
    g)2) phenyl or Het ring, where Het ring is defined as above,
9) —C(O)—R10, in which R10 is defined as above,
10) —S(O)$_p$—R12, in which R12 is defined as above and p is the integers 1 or 2,
11) —$NO_2$,
12) —CN, or
13) —N(R15)-R12, in which R15 is
  13)1) hydrogen atom, or
  13)2) —($C_1$–$C_6$)-alkyl and R12 is defined as above,
X is —OH or —NH—OH,
n1 is the integer 2,
n2 is the integer 3,
R1, R2, R3, R4 and R5 are in each case hydrogen atom.
The invention furthermore relates to the compound of the formula I wherein
A is a covalent bond or —$CH_2$—$CH_2$—,
B, D and E are identical or different and are, independently of each other, —($C_0$–$C_4$)-alkylene or the radical —B1-B2-B3- in which
B1 is —($CH_2$)$_n$—, in which n is the integer zero, 1 or 2,
B3 is —($CH_2$)$_m$—, in which m is the integer zero, 1 or 2, with the proviso that the sum of n and m amounts to zero, 1 or 2, and
B2 is
  1) —C(O)—
  2) —($C_2$–$C_4$)-alkynylene,
  3) —S(O)$_o$—, where o is the integers zero or 1,
  4) —N(R6)-C(Y)—, in which Y is oxygen atom and R6 is hydrogen atom,
  5) —C(Y)—N(R6)-, in which Y is oxygen atom and R6 is hydrogen atom, or
  6) —O—,
ring 1, ring 2 and ring 3 are identical or different and are, independently of each other,
1) covalent bond,
2) phenyl and are unsubstituted or substituted, independently of each other, once or twice, by G, or
3) Het ring, in which the Het ring is a radical from the series furanyl, pyridinyl, pyrimidinyl or thiophenyl, and are unsubstituted or substituted, independently of each other, once or twice, by G,
ring 4 is
1) phenyl and is unsubstituted or substituted, independently of each other, once or twice, by G,
2) Het ring, in which the Het ring is a radical from the series benzofuranyl, dibenzofuranyl, furanyl, 2'-methylbiphenyl-2-ol, morpholinyl, piperazinyl, piperidinyl, pyridinyl, pyrimidinyl, pyridothiophenyl, pyrrolyl, pyrrolidinyl, thiazolyl or thiophenyl and is unsubstituted or substituted, independently of each other, once or twice, by G, or
3) the following radical

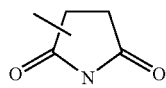

and this radical is unsubstituted or substituted once by G,
G is 1) hydrogen atom,
2) Br, Cl or F,
3) —($C_1$–$C_4$)-alkyl, in which alkyl is unsubstituted or substituted once, twice or three times, by Br, Cl, F, —$C_3$-Cycloalkyl, phenyl or Het ring, where Het ring is defined as above,
4) phenyl,
5) Het ring, where Het ring is defined as above, 6) —C(O)—O—R10, in which R10 is
   a) —(C$_1$–C$_6$)-alkyl, in which alkyl is unsubstituted or substituted, once or twice, by cyclopropyl, phenyl or Het ring, where Het ring is defined as above,
   b) phenyl, or
   c) Het ring, where Het ring is defined as above,
7) —C(O)—NH—R11, in which R11 is
   a) —(C$_1$–C$_6$)-alkyl, in which alkyl is unsubstituted or substituted, once or twice, by cyclopropyl, phenyl or Het ring, where Het ring is defined as above,
   b) phenyl, or
   c) Het ring, where Het ring is defined as above,
8) —O—R12, in which R12 is
   a) hydrogen atom,
   b) —(C$_1$–C$_6$)-alkyl, in which alkyl is unsubstituted or substituted, once, twice or three times, by halogen, cyclopropyl, phenyl or Het ring, where Het ring is defined as above,
   c) phenyl,
   d) Het ring, where Het ring is defined as above,
   e) —C(O)—O—R13, in which R13 is
      e)1) —(C$_1$–C$_6$)-alkyl, in which alkyl is unsubstituted or substituted, once or twice, by cyclopropyl, phenyl or Het ring, where Het ring is defined as above, or
      e)2) phenyl or Het ring, where Het ring is defined as above,
   f) —C(S)—O—R13, in which R13 is defined as above, or
   g) —C(O)—NH—R14, in which R14 is
      g)1) —(C$_1$–C$_6$)-alkyl, in which alkyl is unsubstituted or substituted, once or twice, by phenyl or Het ring, where Het ring is defined as above, or
   g)2) phenyl or Het ring, where Het ring is defined as above,
9) —C(O)—R10, in which R10 is defined as above,
10) —S(O)$_p$—R12, in which R12 is defined as above and p is the integers zero, 1 or 2,
11) —NO$_2$,
12) —CN, or
13) —N(R15)-R12, in which R15 is
   13)1) hydrogen atom, or
   13)2) —(C$_1$–C$_6$)-alkyl and R12 is defined as above,
X is —NH—OH,
n1 is the integer 2,
n2 is the integer 3, and
R1, R2, R3, R4 and R5 are in each case hydrogen atom.

DETAILED DESCRIPTION OF THE INVENTION

The invention also relates to the compound of the formula I from the series,
2-(4'-nitrobiphenyl-4-sulfonyl)decahydroisoquinoline-1-(N-hydroxy)carboxamide;
2-(4'-chlorobiphenyl-4-sulfonyl)decahydroisoquinoline-1-carboxylic acid;
2-(4'-chlorobiphenyl-4-sulfonyl)decahydroisoquinoline-1-(N-hydroxy)-carboxamide;
2-(6-phenoxypyridine-3-sulfonyl)decahydroisoquinoline-1-carboxylic acid trifluoroacetate;
2-(6-phenoxypyridine-3-sulfonyl)decahydroisoquinoline-1-(N-hydroxy)-carboxamide trifluoroacetate;
2-[2-(4'-chlorobiphenyl-4-yl)ethanesulfonyl]decahydroisoquinoline-1-carboxylic acid;
2-[2-(4'-chlorobiphenyl-4-yl)ethanesulfonyl]decahydroisoquinoline-1-(N-hydroxy)carboxamide;
2-[4-(pyridin-4-yloxy)benzenesulfonyl]decahydroisoquinoline-1-carboxylic acid trifluoroacetate;
2-[4-(pyridin-4-yloxy)benzenesulfonyl]decahydroisoquinoline-1-(N-hydroxy)carboxamide trifluoroacetate;
2-[4-(4-methoxyphenoxy)benzenesulfonyl]decahydroisoquinoline-1-carboxylic acid;
2-[4-(4-methoxyphenoxy)benzenesulfonyl]decahydroisoquinoline-1-(N-hydroxy)carboxamide;
2-{4-[4-(2,2,2-trifluoroethoxy)phenoxy]benzenesulfonyl}decahydroisoquinoline-1-carboxylic acid;
2-{4-[4-(2,2,2-trifluoroethoxy)phenoxy]benzenesulfonyl}decahydroisoquinoline-1-(N-hydroxy)carboxamide;
2-[4'-(2,2,2-trifluoroethoxy)biphenyl-4-sulfonyl]decahydroisoquinoline-1-carboxylic acid;
2-(4'-isopropoxycarbonylaminobiphenyl-4-sulfonyl)decahydroisoquinoline-1- carboxylic acid;
[4'-(1-hydroxycarbamoyloctahydroisoquinoline-2-sulfonyl)biphenyl4-yl]carboxamide isopropyl ester;
2-[4'-(2,2,2-trifluoroethoxy)biphenyl-4-sulfonyl]decahydroisoquinoline-1-(N-hydroxy)carboxamide;
2-(4'-trifluoromethoxybiphenyl-4-sulfonyl)decahydroisoquinoline-1-(N-hydroxy)carboxamide;
2-[4-(4-fluorophenoxy)benzenesulfonyl]decahydroisoquinoline-1-(N-hydroxy)carboxamide;
2-[4-(4-trifluoromethoxyphenoxy)benzenesulfonyl]decahydroisoquinoline-1-(N-hydroxy)carboxamide;
2-[4-(4-trifluoromethoxyphenoxy)benzenesulfonyl]decahydroisoquinoline-1-carboxylic acid;
2-(biphenyl-4-sulfonyl)decahydroisoquinoline-1-(N-hydroxy)carboxamide;
2-(biphenyl-4-sulfonyl)decahydroisoquinoline-1-carboxylic acid;
2-[4-(4-cyanophenoxy)benzenesulfonyl]decahydroisoquinoline-1-(N-hydroxy)carboxamide;
2-(dibenzofuran-2-sulfonyl)decahydroisoquinoline-1-carboxylic acid;
2-(dibenzofuran-2-sulfonyl)decahydroisoquinoline-1-(N-hydroxy)carboxamide; or
2-[4-(4-fluorophenoxy)benzenesulfonyl]-6-methoxydecahydroisoquinoline-1-(N-hydroxy)carboxamide, and also all the isomeric forms of the abovementioned compounds.

Definition of Terms

As used above, and throughout the description of the invention, the following terms, unless otherwise indicated, shall be understood to have the following meanings.

The term "physiologically tolerable", or physiologically tolerated" salt is meant to include non toxic salts that are physiologically acceptable, or suitable. In particular, a pharmaceutically utilizable salt.

The term "pharmaceutically effective amount" is meant to describe an amount of a compound, composition, medicament or other active ingredient effective in producing the desired therapeutic effect.

The term "(C$_1$–C$_6$)alkyl" is understood as meaning hydrocarbon radicals whose carbon chain is straight-chain or branched and contains from 1 to 6 carbon atoms, for example methyl, ethyl, propyl, isopropyl, butyl, isobutyl, tertiary butyl, pentyl, isopentyl, neopentyl, hexyl, 2,3-dimethylbutane or neohexyl.

The term "—(C$_0$–C$_4$)alkylene" is understood as meaning hydrocarbon radicals whose carbon chain is straight-chain or branched and contains from 1 to 4 carbon atoms, for example methylene, ethylene, propylene, isopropylene, isobutylene, butylene or tertiary butylene. "—$C_0$-Alkylene" is a covalent bond.

The term "—$(CH_2)_n$—, in which n is the integer zero, 1 or 2" is understood as meaning a covalent bond, where n is zero, the radical methylene, where n is 1 and the radical ethylene where n is 2.

The term "—$(C_2–C_4)$-alkenylene" is understood as meaning hydrocarbon radicals whose carbon chain is straight-chain or branched and contains from 2 to 4 carbon atoms and which, depending on chain length, possess one or two double bonds, for example ethenylene, propenylene, isopropenylene, isobutenylene or butenylene; insofar as the possibility exists in principle, the substituents at the double bond can be arranged in the E position or Z position.

The term "—$(C_2–C_6)$-alkynylene" is understood as meaning hydrocarbon radicals whose carbon chain is straight-chain or branched and contains from 2 to 6 carbon atoms and which, depending on chain length, possess one or two triple bonds, for example ethynylene, propenylene, isopropynylene, isobutynylene, butynylene, pentynylene or isomers of pentynylene, or hexynylene or isomers of hexynylene.

The term "$(C_3–C_6)$-cycloalkyl" is understood as meaning radicals such as compounds which are derived from 3- to 6-membered monocycles such as cyclopropyl, cyclobutyl, cyclopentyl or cyclohexyl.

The radicals

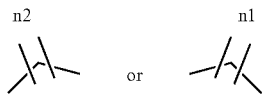

are in each case understood as meaning —$CH_2$— radicals in the ring of the formula I, where the variables n1 or n2 in each case specify the number of the —$CH_2$— radicals in the ring of the formula I. When n1 has the value zero, a covalent bond ensues and the resulting part ring has a total of 4 ring atoms. When n2 has the value zero, a covalent bond ensues and the resulting part ring has a total of 3 ring atoms. When n1 has the value 1, a —$CH_2$— radical ensues and the resulting part ring has a total of 5 ring atoms. When n1 has the value 2, a —$CH_2$—$CH_2$— radical ensues and the resulting part ring has a total of 6 ring atoms. When n1 has the value 3, a —$CH_2$—$CH_2$—$CH_2$— radical ensues and the resulting part ring has a total of 7 ring atoms. Corresponding part rings ensue in the case of n2.

The term "—$(C_6–C_{14})$-aryl" is understood as meaning aromatic hydrocarbon radicals having from 6 to 14 carbon atoms in the ring. —$(C_6–C_{14})$-Aryl radicals are, for example, phenyl, naphthyl, for example 1-naphthyl or 2-naphthyl, anthryl or fluorenyl. Naphthyl radicals and, in particular, phenyl radicals are preferred aryl radicals.

The term "4- to 15-membered Het ring" or "Het ring" is understood as meaning ring systems which have from 4 to 15 carbon atoms, which are present in one, two or three ring systems which are linked to each other, and which contain one, two, three or four identical or different heteroatoms from the series oxygen, nitrogen or sulfur. Examples of these ring systems are the radicals acridinyl, azepinyl, azetidinyl, aziridinyl, benzimidazalinyl, benzimidazolyl, benzofuranyl, benzothiofuranyl, benzothiophenyl, benzoxazolyl, benzothiazolyl, benzotriazolyl, benzotetrazolyl, benzisoxazolyl, benzisothiazolyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, dibenzofuranyl, dibenzothiophenyl, dihydrofuran[2,3-b]tetrahydrofuranyl, dihydrofuranyl, dioxolyl, dioxanyl, 2H,6H-1,5,2-dithiazinyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolidinyl, 2-isothiazolinyl, isothiazolyl, isoxazolyl, isoxazolidinyl, 2-isoxazolinyl, 2'-methylbiphenyl-2-ol, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxothiolanyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyroazolidinyl, pyrazolinyl, pyrazolyl, pyridazinyl, pyridooxazolyl, pyridoimidazolyl, pyridothiazolyl, pyridothiophenyl, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrahydropyridinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiomorpholinyl, thiophenyl, triazinyl, 1,2,3-triazolyl, 1,2,4-triazolyl, 1,2,5-triazolyl, 1,3,4-triazolyl and xanthenyl.

Preferred Het rings are the radicals benzofuranyl, benzimidazolyl, benzoxazolyl, benzothiazolyl, benzothiophenyl, 1,3-benzodioxolyl, quinazolinyl, quinolinyl, quinoxalinyl, chromanyl, cinnolinyl, furanyl such as 2-furanyl and 3-furanyl; imidazolyl, indolyl, indazolyl, isoquinolinyl, isochromanyl, isoindolyl, isothiazolyl, isoxazolyl, 2'-methylbiphenyl-2-ol, oxazolyl, phthalazinyl, pteridinyl, pyrazinyl, pyrazolyl, pyridazinyl, pyridoimidazolyl, pyridopyridinyl, pyridopyrimidinyl, pyridyl; such as 2-pyridyl, 3-pyridyl or 4-pyridyl; pyrimidinyl, pyrrolyl; such as 2-pyrrolyl and 3-pyrrolyl; purinyl, thiazolyl, tetrazolyl or thienyl; such as 2-thienyl and 3-thienyl.

The term "halogen" is understood as meaning fluorine, chlorine, bromine or iodine.

The invention furthermore relates to a process for preparing the compound of the formula I and/or a stereoisomeric form of the compound of formula I and/or a physiologically tolerated salt of the compound of the formula I, which comprises a) reacting a compound of the formula IV,

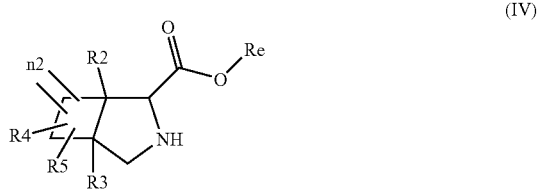

in which Re is a hydrogen atom or an ester-protecting group, with a compound of the formula V,

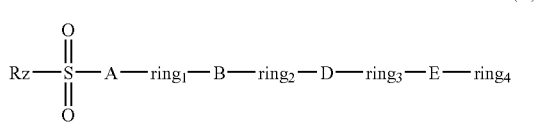

in which A, B, D, E and ring 1, ring 2, ring 3 and ring 4 are defined as in formula I, and in which Rz is chlorine atom, imidazoyl or OH, in the presence of a base or following silylation with a suitable silylating agent, or using a suitable dehydrating agent when Rz=OH, to give a compound of the formula VI,

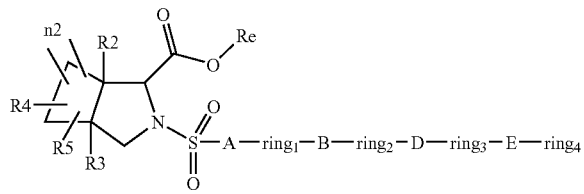

(VI)

in which A, B, D, E, Re and ring 1, ring 2, ring 3 and ring 4 are defined as above, and b) when Re=ester reacting a compound of the formula VI prepared as described in a) with a solution of alkali such as NaOH or LiOH, and then treating the product with acid, to give the carboxylic acid according to the invention of the formula I, in which X=OH (corresponding to VII), with modifications in one of the side chains of the rings ring 1-ring 4 also having previously been made, where appropriate; or converting said ester, by treating it with a mineral acid, such as hydrochloric acid, into the free carboxylic acid VII

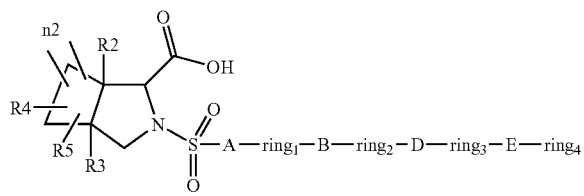

(VII)

and then converting this into the hydroxamic acid according to the invention, in which X=NH—OH, of the formula I, c) using salt formation with enantiomerically pure acids or bases, chromatography on chiral stationary phases, or derivatization with chiral, enantiomerically pure compounds such as amino acids, separation of the resulting diastereomers and elimination of the chiral auxiliary groups, to separate a compound of formula I prepared as described in procedure a), or a suitable precursor of the formula I, which arises in enantiomeric forms due to its chemical structure, into the pure enantiomers, or d) either isolating the compound of the formula I prepared as described in procedures b) or c) in free form, or, when acid or basic groups are present, converting it into physiologically tolerated salts.

Compounds of the formula IV to VII type are compounds which are only presented by way of example; in accordance with formula I, it is also possible to adduce four-membered rings, six-membered rings and seven-membered rings instead of the five-membered ring.

Compounds of the formula IV type can be prepared using known protocols. For example, compounds in which $n_1=1$ and $n_2=0$ (methanoprolines) can be prepared using a number of known methods. The description of a recent synthesis can be found, for example, in Tetrahedron 53, 14773–92 (1997).

For example, the bicyclic skeletons of the formula IV in which $n_1=2$ and $n_2=3$ in accordance with formula I can be prepared by hydrogenation of isoquinoline-1-carboxylic acid or suitable derivatives of isoquinoline-1-carboxylic acid, such as methyl ester or ethyl ester. This hydrogenation is described, for example, in U.S. Pat. No. 5,430,023, U.S. Pat. No. 5,726,159 and EP 643073.

In the same way, it is possible to use 1,2,3,4-tetrahydroisoquinoline-1-carboxylic acid and its derivatives to prepare these compounds by hydrogenation. This procedure has the advantage that it is possible to use a broad range of methods for synthesizing the 1,2,3,4-tetrahydroisoquinoline-1-carboxylic acids. For example, Pictet-Spengler-type cyclizations, such as described in U.S. Pat. No. 4,902,695, are particularly well known and broadly applicable. Depending on the nature of the starting compounds employed, such methods can be used, for example, to obtain substituted compounds, i.e. compounds in which the substituents R1, R4 and R5 are not H atoms. A novel example of ring-substituted compounds can be found in WO 200304/1641. Innumerable examples of R1 and/or R4 and R5 not being H exist and are readily available to the skilled person.

Other possible methods for preparing the cyclic skeletons use free radical cyclization reactions, for example, and are described in Tetrahedron 48, 4659–76 (1992).

Other methods can be used for synthesizing compounds of the IV type when $n_1=1$ and $n_3=3$. For example, described syntheses are to be found in Tetrahedron 55, 8025 (1999) and Tetrahedron Lett. 24, 5339 (1983) or in the laid-open specifications DE 3322530 and DE 3211676.

Methods for synthesizing compounds of the IV type in which $n_1=1$ and $n_2=2$ are likewise to be found in Tetrahedron 55, 8025 (1999) and DE 3322530 or DE 3211676.

Methods for synthesizing the skeletons of related compounds, for example in which $n_1=1$ and $n_2=4$, are also described. For example, J. Org. Chem. 61, 7125 (1996) describes syntheses of β-lactams which contain said skeleton. The substituted basic structures in analogy with formula IV can also be prepared from these compounds by opening the β-lactam.

Methods for synthesizing the skeletons in which $n_1=2$ and $n_2=4$ are likewise known and well described, for example in EP 0672665 and the abovementioned references. The groups used as protecting groups for esters in "Protective Groups in Organic Synthesis", T. H. Greene, P. G. M. Wuts, Wiley-Interscience, 1999, can be used as the ester-protecting group Re. Examples of preferred ester-protecting groups are methyl, ethyl, isopropyl, tert-butyl and benzyl.

Under certain conditions, it can be useful to employ compounds of the IV type in the N-protected state. For example, it is easier to purify compounds which are protected in this way than it is to purify the free imino acids; in the same way, these protected compounds can sometimes also be more readily used for preparing the enantiomerically pure or diastereomerically pure compounds. The groups described in "Protective Groups in Organic Synthesis", T. H. Greene, P. G. M. Wuts, Wiley-Interscience, 1999, can be employed as protecting groups for the amino group. Examples of preferred amino-protecting or imino-protecting groups are Z, Boc, Fmoc, Aloc, acetyl, trifluoroacetyl, benzoyl, benzyl and the like.

The starting compounds and reagents employed can either be prepared using known methods or obtained commercially.

The reactions are carried out as described, for example, in WO 97/18194. The reaction as described in procedural step a) takes place in the presence of a base, such as KOH, NaOH, LiOH, N-methylmorpholine (NMM), N-ethylmorpholine (NEM), triethylamine (TEA), diisopropylethylamine (DIPEA), pyridine, collidin, imidazole or sodium carbonate, in solvents such as tetrahydrofuran (THF), dimethylformamide (DMF), dimethylacetamide, dioxane, acetonitrile, toluene, chloroform or methylene chloride, or else in the presence of water. If the reaction is being carried out using silylating agents, N,O-bis(trimethylsilyl)acetamide (BSA) or N,O-bis(trimethylsilyl)-trifluoroacetamide (BSTFA) is used, for example, for silylating the imino acid in order to subsequently carry out the sulfonamide formation.

Modifications in the side chain mean that, for example, a nitro group is hydrogenated using the metal catalyst Pd/C, or reacted with $SnCl_2$ or Zn under standard conditions, and the resulting amino group can then be subjected to further modification, for example by reacting it with carbonyl chlorides, sulfonyl chlorides, chloroformic esters, isocyanates, isothiocyanates or other reactive or activatable reagents in order to arrive at the precursors of the compounds of formula I according to the invention. In this case, it is frequently advantageous for Re in compound VI to be an ester since side reactions can be expected when the carboxylic acid is unprotected.

In procedural step c), the compound of the formula I is separated, insofar as it arises as a mixture of diastereomers or enantiomers, or accrues in the chosen synthesis as their mixtures, into the pure stereoisomers, either by means of chromatography on a support material, which is chiral where appropriate, or, provided the racemic compound of formula I is capable of salt formation, by means of fractional crystallization of the diastereomeric salts which are formed with an optically active base or acid used as auxiliary substance. Examples of chiral stationary phases which are suitable for separating enantiomers by means of thin layer chromatography or column chromatography are modified silica gel supports (what are termed Pirkle phases) and also high molecular weight carbohydrates such as triacetylcellulose. For analytical purposes, it is also possible, following appropriate derivatization known to the skilled person, to use gas-chromatographic methods on chiral stationary phases. In order to resolve the racemic carboxylic acids into their enantiomers, an optically active base, which is as a rule commercially available, such as (−)-nicotine, (+)- and (−)-phenylethylamine, quinine bases, L-lysine or L- and D-arginine, are used to form the differently soluble diastereomeric salts, the more difficulty soluble component is isolated as a solid, the more readily soluble diastereomer is removed from the mother liquor, and the pure enantiomers are obtained from the diastereomeric salts which have thus been isolated. In what is in principle the same way, the racemic compounds of the formula I which contain a basic group such as an amino group can be converted into the pure enantiomers using optically active acids, such as (+)-camphor-10-sulfonic acid, D- and L-tartaric acid, D- and L-lactic acid and also (+)- and (−)-mandelic acid. It is also possible to convert chiral compounds which contain alcohol or amine functions into the corresponding esters or amides using appropriately activated and, where appropriate, N-protected enantiomerically pure amino acids or, vice versa, to convert chiral carboxylic acids into the amides using carboxyl-protected enantiomerically pure amino acids or to convert them into the corresponding chiral esters using enantiomerically pure hydroxycarboxylic acids such as lactic acid. The chirality of the amino acid radical or alcohol radical which has been introduced in enantiomerically pure form can then be used for separating the isomers by carrying out a separation of the diastereomers, which are now present, by means of crystallization or by means of chromatography on suitable stationary phases and, after that, using suitable methods to once again eliminate the entrained chiral molecule moiety.

In addition, the possibility arises, in the case of some of the compounds according to the invention, of using diastereomerically pure or enantiomerically pure starting compounds for preparing the skeletal structures. This then makes it possible, where appropriate, to also use other methods, or simplified methods, for purifying the end products. These starting compounds were prepared beforehand in enantiomerically pure form or diastereomerically pure form using methods known from the literature. For example, it is possible, as mentioned and cited above, to use isoquinoline-1-carboxylic acid directly in the method for preparing decahydroisoquinoline-1-carboxylic acid. As a result of 3 heterocenters being present, it is possible, in this case, to form a maximum of 8 stereoisomers (4 enantiomeric diastereomer pairs). However, the nature of the preparation, for example hydrogenation, strongly favors certain stereoisomers. Thus, it should be possible, as described in the literature, to achieve strong preference for hydrogen attachment at the positions of the ring linkage, for example, by selecting the hydrogenation conditions (catalyst, pressure, solvent and temperature) appropriately. Thus, it is possible, under the specified conditions, to achieve formation of the cis-linked rings. It would then consequently only remain a matter of determining the position of the carboxylic acid since the number of possible stereoisomers would already be restricted to 4. As a result of the nature of the hydrogenation mechanism, it is particularly easy to attach the hydrogens on the same side as that of the bridgehead hydrogens, i.e. a further restriction in the possibility of isomer formation is thereby to be expected. It would consequently be possible, in the most favorable case, to assume that only one enantiomer pair would be formed. It ought then to be possible to use the abovementioned methods to resolve this pair into the enantiomers. However, in connection with these considerations, it has also to be assumed that complete stereoselection will never take place and that, on the contrary, varying proportions of the other isomers will virtually always also be formed or will be detectable, even in very small quantities, when suitable methods are used. When enantiomerically pure 1,2,3,4-tetrahydroisoquinoline-1-carboxylic acid derivatives are used, it would be expected that, if the reaction conditions were identical or similar to those used during the hydrogenation of isoquinoline-1-carboxylic acid, analogous considerations would apply and it would once again to a large extent only be preferred stereoisomers which were formed; in this said case, there should be strong preference for only one single enantiomer since, when carrying out the hydrogenation process under conditions which were analogous to those which lead to the cis ring linkage when hydrogenating isoquinoline-1-carboxylic acid, the H atoms can once again only be attached from the one side and, as a consequence, analogous products will be formed. The identity of the structures can be established by means of suitable 2D NMR experiments, X ray methods such as cocrystallization and others, as well as reference analysis or chemical derivatization and suitable analysis or chemical derivatization which leads to known and described isomers.

Another possibility for synthesizing enantiomerically pure or diastereomerically pure compounds is that of using suitably chirally substituted starting compounds in order, by means of the chiral substituent, to achieve induction of chirality at other chiral centers. For example, chiral glyoxylic esters could be used in Pictet-Spengler cyclizations in order to obtain chiral Tic derivatives and then to hydrogenate these derivatives, as already mentioned above.

Acid or basic products of the compound of formula I can be present in the form of their salts or in free form. Preference is given to pharmacologically tolerated salts, for example alkali metal or alkaline earth metal salts, or hydrochlorides, hydrobromides, sulfates, hemisulfates and all possible phosphates, as well as salts of the amino acids, natural bases or carboxylic acids. Physiologically tolerated salts are prepared in a manner known per se, in accordance with procedural step d), from compounds of formula I, including their stereoisomeric forms, which are capable of salt formation. The compounds of formula I form stable alkali metal salts, alkaline earth metal salts, or optionally substituted ammonium salts, with basic reagents such as hydroxides, carbonates, hydrogen carbonates or alkoxides, as well as ammonia or organic bases, for example trimethylamine, triethylamine, ethanolamine, diethanolamine, triethanolamine or trometamol, or else basic amino acids, for example lysine, ornithine or arginine. Provided the compounds of formula I possess basic groups, it is also possible to prepare stable acid addition salts using strong acids. Both inorganic and organic acids, such as hydrochloric acid, hydrobromic acid, sulfuric acid, hemisulfuric acid, phosphoric acid, methanesulfonic acid, benzenesulfonic acid, p-toluenesulfonic acid, 4-bromobenzenesulfonic acid, cyclohexylamidosulfonic acid, trifluoromethylsulfonic acid, 2-hydroxyethanesulfonic acid, acetic acid, oxalic acid, tartaric acid, succinic acid, phosphoglyceric acid, lactic acid, malic acid, adipic acid, citric acid, fumaric acid, maleic acid, gluconic acid, glucuronic acid, palmitic acid or trifluoroacetic acid are suitable for this purpose.

The invention also relates to pharmaceuticals which are characterized by an effective content of at least one compound of the formula I and/or a physiologically tolerated salt of the compound of formula I and/or an optionally stereoisomeric form of the compound of formula I, together with a pharmaceutically suitable and physiologically tolerated carrier substance, additive and/or other active compounds and auxiliary substances.

On account of their pharmacological properties, the compounds according to the invention are suitable for the selective prophylaxis and therapy of all those diseases whose course involves an increase in the activity of the metalloproteinases. These diseases include degenerative joint diseases such as osteoarthroses, spondyloses and chondrolysis following joint trauma or a relatively long period of joint immobilization following meniscus injuries or patella injuries or ligament ruptures. They furthermore also include diseases of the connective tissue such as collagenoses, periodontal diseases, wound healing disturbances and chronic diseases of the locomotory apparatus such as inflammatory, immunologically determined or metabolism-determined acute and chronic arthritides, arthropathies, myalgias and disturbances of bone metabolism. The compounds of the formula I are furthermore suitable for the treatment of ulceration, atherosclerosis and stenoses. In addition, the compounds of the formula I are suitable for the treatment of inflammations, cancer diseases, tumor metastases formation, cachexia, anorexia, heart failure and septic shock. The compounds are also suitable for the prophylaxis of myocardial and cerebral infarctions.

The pharmaceuticals according to the invention can be administered by means of oral, inhalative, rectal or transdermal administration or by means of subcutaneous, intraarticular, intraperitoneal or intravenous injection. Oral administration is preferred.

The invention also relates to a process for producing a pharmaceutical, which comprises bringing at least one compound of the formula I, together with a pharmaceutically suitable and physiologically tolerated excipient and, where appropriate, other suitable active compounds, additives or auxiliary substances, in a suitable form of administration.

Examples of suitable solid or galenic preparation forms are granules, powders, sugar-coated tablets, tablets, (micro) capsules, suppositories, syrups, juices, suspensions, emulsions, drops or injectable solutions, as well as preparations giving a protracted release of active compound, the production of which makes use of customary adjuvants such as carrier substances, disintegrants, binders, coating agents, swelling agents, glidants, lubricants, flavorings, sweeteners and solubilizers. Frequently employed auxiliary substances which may be mentioned are magnesium carbonate, titanium dioxide, lactose, mannitol and other sugars, talc, milk protein, gelatin, starch, cellulose and its derivatives, animal and vegetable oils, such as cod liver oil, sunflower oil, groundnut oil or sesame oil, polyethylene glycol and solvents such as sterile water and monohydric or polyhydric alcohols, such as glycerol.

The pharmaceutical preparations are preferably produced and administered in dosage units, with each unit containing, as the active constituent, a defined dose of the compound of the formula I according to the invention. This dose can be up to about 1000 mg, preferably, however, from about 50 to 300 mg, in the case of solid dosage units, such as tablets, capsules, sugar-coated tablets or suppositories, and be up to about 300 mg, preferably, however, from about 10 to 100 mg, in the case of injection solutions in ampoule form.

Daily doses of from about 2 mg to 1000 mg of active compound, preferably of from 50 mg to 500 mg, are indicated, in dependence on the activity of the compound of the formula I, for treating an adult patient weighing about 70 kg. However, higher or lower daily doses may sometimes also be appropriate. The daily dose can be administered either by means of a once-only administration in the form of a single dosage unit or of several smaller dosage units or else by means of the multiple administration of subdivided doses at defined intervals.

End products are as a rule determined by means of mass-spectroscopic methods (FAB-MS and ESI-MS) and $^1$H-NMR (400 MHz, in DMSO-D6); the main peak or the two main peaks are given in each case. Temperatures are given in degrees centigrade, RT denotes room temperature (21° C. to 24° C.). The abbreviations employed are either explained or in conformity with the customary conventions. The invention is clarified below with the aid of examples.

The following examples are intended to illustrate but not limit the present invention.

EXAMPLES

General Protocol 1

Sulfonamide From sulfonyl chloride and carboxylic acid

The carboxylic acid (6.45 mmol) was dissolved in 20 ml of dimethylformamide (DMF), and 3 equivalents of a 3N solution of NaOH (6.45 ml) were added at 0° C. After 10 min, a solution of the arylsulfonyl chloride (1.1 equivalents, 7.1 mmol) in from 10 to 15 ml of DMF was slowly added dropwise; after room temperature (RT) has been reached, the mixture continues to be stirred for a maximum of 12 hours (h) at temperatures between 20° C. and 80° C. The precise time depends on when conversion is complete, with this being established by mass spectroscopy. After that, the solvent was removed under reduced pressure. Aqueous working-up (extracting by shaking with 1N HCl and a saturated solution of NaCl, drying of the organic phase such as ethyl acetate, methylene chloride or chloroform with magnesium sulfate or sodium sulfate, and after that concentrating) subsequently took place. The crude product was either subjected directly to further reaction or purified by chromatography.

General Protocol 2

Sulfonamide From sulfonyl chloride and carboxylic acid

The carboxylic acid was dissolved in 0.5–2 molar NaOH, where appropriate in the added presence of 10–50% tetrahydrofuran (THF) or DMF. Acid chloride (1–1.2 equivalents, preferably 1.1) was dissolved in THF (concentration, from 0.05 to 1 M) and this solution was slowly added dropwise. 2 N NaOH was automatically added at RT, using an autotitrator, for the purpose of maintaining a constant pH. The set pH was: from 8 to 12, preferably from 9 to 11. After the termination of the reaction, recognizable by no further NaOH being consumed, the organic cosolvent was removed on a rotary evaporator and the aqueous solution or suspension was treated with ethyl acetate and acidified with 1N HCl. After the organic phase had been separated off, and the aqueous phase had been extracted once again with ethyl acetate, the organic phases were combined and dried over sodium sulfate; the solvent was subsequently removed under reduced pressure. The crude product was either subjected directly to further reaction or purified by chromatography.

General Protocol 3

Sulfonamide From sulfonyl chloride and carboxylic acid

This protocol is particularly suitable for the reaction of biphenylethylsulfonyl chloride with iminocarboxylic acids (see Example 6 and Example 7) or similar, more hydrolysis-labile sulfonyl chlorides.

8 mmol of the imino acid were dissolved or suspended in 30 ml of acetonitrile. 2.3 g (9 mmol) of BSTFA (bis(trimethylsilyl)trifluoroacetamide) were added at RT and under an inert gas ($N_2$) and the mixture was heated for 2 h under reflux. 2.84 g (9 mmol) of 4-chlorobiphenylethanesulfonyl chloride, dissolved in 30 ml of acetonitrile, were added to this solution and the whole was once again heated for 3 h under reflux conditions. After the reaction mixture had cooled down, aqueous 1 N HCl was added and the mixture was stirred for 1 h; the solvent was then removed under reduced pressure on a rotary evaporator, after which ethyl acetate or chloroform was added; the organic phase was then separated off, extracted with a saturated solution of NaCl, dried over sodium sulfate and concentrated under reduced pressure. Depending on its purity, it was either possible to subject the reaction product directly to further reaction or necessary to previously chromatograph it through silica gel.

General Protocol 4

Preparing the hydroxamic acid From carboxylic acid by Way of chloroformate activation The sulfonated carboxylic acid was dissolved in 10 ml of DMF after which 1.1 equivalents of ethyl chloroformate, 2.2 equivalents of N-ethylmorpholine and, after a preactivation time of from 30 min to 1 h, 3 equivalents of trimethylsilyl-hydroxylamine were added at 0° C. After the mixture had been heated at 80° C. for at least 4 h, the solvent was removed under reduced pressure and the crude product purified using chromatographic methods.

General Protocol 5

Preparing the hydroxamic acid by Way of the Corresponding carbonyl chloride

The sulfonated carboxylic acid was initially introduced in dry chloroform (ethanol-free) (about 5 ml for 0.5 mmol) and 3 equivalents of oxalyl chloride were added at RT. The mixture was then heated at 45° C. for about 30 min. In order to monitor the chloride formation, a small sample was removed from the reaction flask and treated with a little benzylamine in THF. It was possible to ascertain when the reaction was complete by the quantitative formation of benzylamide; it was no longer possible to detect the carboxylic acid (monitoring by HPLC-MS). It may be necessary to heat for a longer period or to heat under reflux conditions. The solvent was then distilled off under reduced pressure, after which the residue was taken up repeatedly in dry toluene and once again subjected to rotary evaporation. The acid chloride was now once again taken up in chloroform (10 ml per 0.5 mmol) and this mixture was treated, at RT, with 3 equivalents of O-trimethylsilylhydroxylamine. After a reaction period of at least 30 min (reaction monitored by HPLC-MS), the reaction mixture was evaporated under reduced pressure and the residue was purified directly by chromatography.

Special Protocol 1

4-Chlorobiphenylethanesulfonyl chloride (Intermediate for Example 7)

Step 1: 1-(2-Bromoethenone)-4-(4-chlorophenyl)benzene
4-Chlorobiphenyl (23.6 g, 0.125 mol) was introduced, in portions and at 0° C., into a stirred suspension of $AlCl_3$ (34.7 g, 0.26 mol) and bromoacetyl bromide (25.2 g, 0.125 mol) in 400 ml of $CS_2$ and the reaction mixture was then heated under reflux for 3 h. After that, it was slowly poured onto ice and subsequently extracted with ethyl acetate; the organic phase was then washed with an aqueous solution of $NaHCO_3$ and with water. It was then dried over anhydrous sodium sulfate and evaporated under reduced pressure. The residue which remained was recrystallized from dichloromethane. Yield: 24.2 g (62% of theory). m.p.: 127–128° C.; $^1$H-NMR: (300 MHz) 5.0 (s, 2H, $CH_2$); 7.5–8.1 (4d, 8H, ar); MS: 311.1 (M+H).

Step 2: 4-Chlorobiphenylethane bromide
tert-Butylamineborane (27.5 g, 0.31 mol) was added, at 0° C., to a stirred suspension of $AlCl_3$ (20.0 g, 0.15 mol) in dichloromethane (500 ml). After the mixture had been stirred at 0° C. for 15 min, a solution of the bromoketone from step 1 (16.0 g, 50 mmol) in dichloromethane (150 ml)

was added and the mixture was stirred at 0° C. for a further 4 h. Cold dilute HCl (1N, 30 ml) was added dropwise, after which the mixture was extracted several times with ethyl acetate. The combined organic phases were washed first with dilute HCl and then with a saturated solution of sodium chloride, after which they were evaporated. An oily compound, which was purified by flash chromatography on silica gel, was obtained. Yield: 15 g (quantitative), m.p.: 142° C.; $^1$H-NMR: (300 MHz) 3.2; 3.78 (2t, 4H, CH$_2$); 7.4–7.7 (4 d, 8H, ar); MS: 296.2 (M+H).

Step 3: Sodium salt of the 4-chlorobiphenylethanesulfonic acid

The compound from step 2 (14.8 g, 50 mmol) was dissolved in a mixture of ethanol and water (1:1, 200 ml). Sodium sulfite (9.5 g, 75 mmol) and tetrabutylammonium iodide (1.8 g, 5 mmol) were added and the mixture was heated under reflux for 16 h. After that, the liquid reaction mixture was decanted off from a small quantity of a solid and the volume of this mixture was reduced by partially evaporating the mixture under reduced pressure. Then the mixture was cooled, the product crystallized out and was subsequently filtered off and recrystallized from MeOH/H$_2$O. It was then dried under reduced pressure. Yield: 13.9 g (94% of theory); $^1$H-NMR: (300 MHz) 2.6; 2.95 (2 m, 4 H, CH$_2$); 7.3–7.7 (4 d, 8H, ar).

Step 4: 4-Chlorobiphenylethanesulfonyl chloride

Phosphorus pentachloride (3.2 g, 15 mmol) was added to a suspension of the compound from step 3 (4.8 g, 15 mmol) in phosphorus oxychloride (50 ml). The mixture was heated at 60° C. for 6 h and was subsequently poured onto ice after methylene chloride had been added. This mixture was neutralized with a saturated solution of sodium hydrogen carbonate and the organic phase was separated off, dried and evaporated under reduced pressure. Yield: 5 g (quantitative); $^1$H-NMR: (300 MHz) 2.9 (m, 4H, CH$_2$); 7.3–7.7 (4 d, 8H, ar).

Using chiral high pressure liquid chromatography (HPLC) to separate the enantiomers of preparation example 3:

Column employed: Chiralpak AD$^R$, 250×4.6 mm, 30° C.; running time: 30 min; injection volume: 5 μl; flow rate: 1 ml/min; solvent MeOH/EtOH 1:1 isocratic; detection at 277 nm. isomer 1 (example 14): running time (RT) 6.33 min, 50.48% and isomer 2 (example 15): RT 14.65 min, 49.52%.

Two-dimensional NMR spectroscopy was used to determine the structure of isomer I. The methodology only makes it possible to determine the relative stereochemistry, i.e. the positions of the chiral centers in relation to each other. This means that, when only one single enantiomer is present, as is to be expected after an enantiomer separation, this enantiomer can have either the absolute stereochemistry which is specified or else the absolute stereochemistry which is the mirror image to it. The final structural proof can only be obtained by carrying out X-ray structural analyses. This was done both by means of cocrystallizing with MMP-13 and by means of a single-crystal structural analysis. Both methods showed unambiguously that the stereochemistry which is specified is in accordance with the actual stereochemistry, Chiral HPLC can likewise be used to carry out chiral separations of the other compounds which represent such enantiomeric mixtures, i.e. which have been prepared from the same decahydroisoquinoline derivatives.

Table 1 shows the results:

TABLE 1

Chemical shift of isomer 1 at 300K.

Molecular Weight = 448.97
Exact Mass = 448
Molecular Formula = C22H25ClN2O4S

| No. | $^1$H | $^{13}$C |
|---|---|---|
| 1 | 4.12 | 55.15 |
| 2 | 1.93 | 35.68 |
| 3 | 1.67/1.41 | 26.37 |
| 4 | 1.19 | 21.03 |
| 5 | 1.48/1.16 | 24.26 |
| 6 | 1.86/1.12 | 26.06 |
| 7 | 1.52 | 32.00 |
| 8 | 1.55/1.45 | 28.88 |
| 9 | 3.75/3.53 | 38.95 |
| 10 | — | 138.99 |
| 11 | 7.81 | 127.29 |
| 12 | 7.87 | 127.26 |
| 13 | — | 142.45 |
| 14 | — | 137.19 |
| 15 | 7.78 | 128.81 |
| 16 | 7.57 | 129.05 |
| 17 | — | 133.42 |
| 18 | — | 166.96 |
| 18-NH | 10.86 | — |
| 18-NOH | 8.88 | — |

Preparation Example 1

N-(4-Chlorobiphenylsulfonyl)decahydroisoquinoline-1-carboxylic acid

Decahydroisoquinolinecarboxylic acid was prepared and used as described in U.S. Pat. No. 5,430,023. The resulting imino acid (2.0 g, 9.1 mmol) was dissolved or suspended in THF (20 ml) and the pH was adjusted to 10.5 with 1 molar sodium hydroxide solution using an autotitrator. After that, 4-chlorobiphenylsulfonyl chloride (2.745 g, 9.6 mmol, 1.05 eq.), dissolved in 10 ml of THF, was added dropwise over a period of 2 hours while the pH was maintained constant. After a further 2 hours, it was not possible to observe any further consumption of sodium hydroxide solution. LC-MS, which was carried out as a reaction control, confirmed this. The solution was then adjusted to a pH of from 3 to 4 with dilute hydrochloric acid; 100 ml of ethyl acetate were then added and the solution was extracted by being shaken. The aqueous phase was extracted a further 2 times with small portions of ethyl acetate and the combined organic phases were dried over sodium sulfate. After the solvent had been removed, there then remained an oily residue which became solid under an oil pump vacuum. Yield: 2.31 g (58% of theory). Analytical data: see Table 1.

Preparation Example 2

N-(4-Chlorobiphenylsulfonyl)decahydroisoquinoline-1-(N-hydroxy)carboxamide

The carboxylic acid from Example 2 (2.3 g, 5.3 mmol) was dissolved in 50 ml of chloroform. Oxalyl chloride (1.345 g, 10.6 mmol, 0.924 ml) was then added dropwise within the space of 10 min and the resulting reaction mixture was heated at 45° C. for one hour. After this time, a small sample of the reaction mixture (0.1 ml) was removed, for monitoring the reaction by HPLC-MS, and treated with 0.05 ml of benzylamine. Subsequently, the solvent was distilled off under reduced pressure and the resulting oily residue was entrained with toluene for the purpose of removing any possible oxalyl chloride residues or HCl and left under reduced pressure for 15 min. It was then once again taken up in chloroform (50 ml) after which O-trimethylsilylhydroxylamine (2.23 g, 21.2 mmol, 2.593 ml) was added at RT. After 2 hours, the solvent was removed under reduced pressure and the residue was dissolved in a small quantity of a mixture of acetonitrile/water/0.01% trifluoroacetic acid for the purpose of direct preparative RP-HPLC. Product fractions were combined, acetonitrile was removed under reduced pressure and the remaining aqueous phase was freeze-dried. Yield: 749 mg (32% of theory; 36 mg of another diastereomer of the same molar mass is obtained in addition). Unreacted acid chloride was reisolated in the form of the carboxylic acid. Analytical data: see Table 1.

The following examples were prepared in analogy with the previously mentioned protocols.

Table 2 shows the results.

TABLE 2

| Example | Structure | Molecular Weight | ES$^+$ | 1H-NMR |
|---------|-----------|------------------|--------|--------|
| 1 | 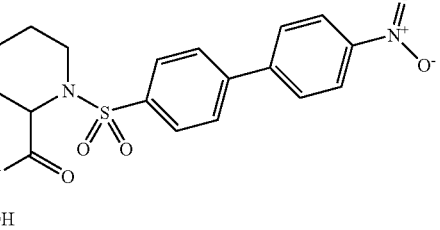 | 459.52 | 460.2<br>461.2 | 1.1–2.0 (4m, 12H); 3.5–3.9 (m, 2H); 4.15 (d, 1H); 7.88; 8.0; 8.07; 8.35 (4d, 8H); 10.9 (s, 1H) |
| 2 | 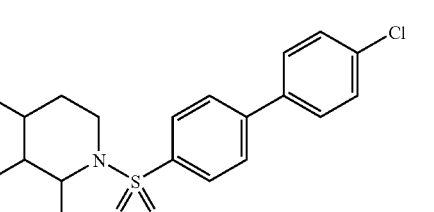 | 433.95 | 433.11 | 1.2–2.1 (4m, 12H); 3.4–3.6 (m, 2H); 4.2 (d, 1H); 7.60; 7.8; (2d, 4H); 7.9 (m, 4H); 12.8 (s, 1H) |
| 3 | 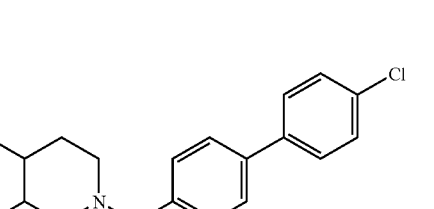 | 448.97 | 449.15<br>451.10 | 1.1–2.0 (4m, 12H); 3.5–3.9 (m, 2H); 4.15 (d, 1H); 7.60; 7.7; 7.8; 7.9(4d, 8H); 10.9 (s, 1H) |
| 4 | 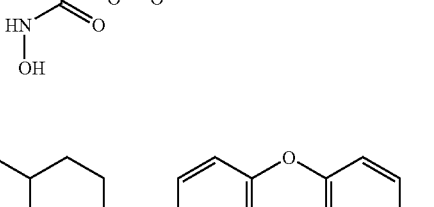 | 530.52 | 415.16 (ES-) | |

TABLE 2-continued

| Example | Structure | Molecular Weight | ES+ | 1H-NMR |
|---|---|---|---|---|
| 5 | 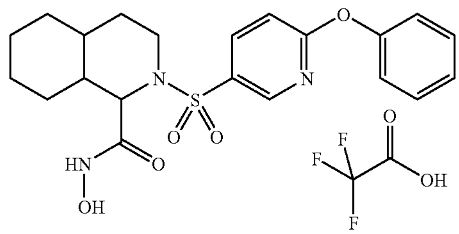 | 545.54 | ES- 430.17 | 1.1–2.0 (4m, 12H); 3.4–3.8 (2m, 2H); 4.08 (d, 1H); 7.2 (m, 4H); 7.45 (m, 2H); 8.1 (dd, 1H); 8.45 (s, 1H); 10.8 (s, 1H) |
| 6 | 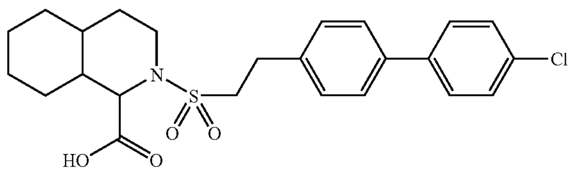 | 462.01 | 461.14 | 1.15–2.05 (4m, 12H); 2.9–3.5 (mm, about 6H, overlapping with water); 3.85 (m, 1H); 4.0 (d, 1H); 7.48; 7.5; 7.61; 7.7 (4d, 8H) |
| 7 | 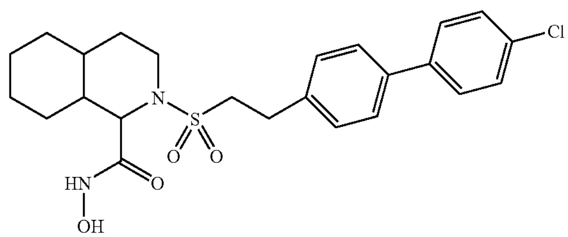 | 477.03 | 477.7 | 1.15–2.05 (mm, 12H); 2.9–3.5 (mm, about 6 H, overlapping with water); 4.85 (m, 1H); 7.48; 7.5; 7.65; 7.72 (4d, 8H) |
| 8 | 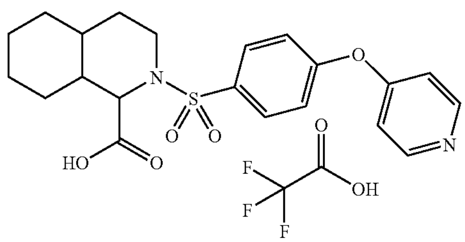 | 530.52 | 416.14 | 1.2–2.1 (4m, 12H); 2.9–4.3 (mm, about 3H, overlapping with water); 7.3; 7.45; 7.95; 8.70 (4m, 8H); 12.8 (s, 1H) |
| 9 | 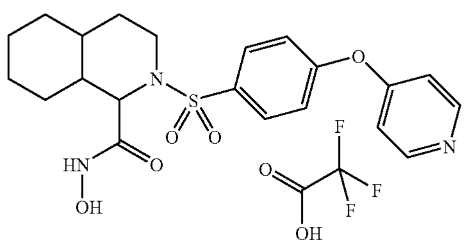 | 545.54 | 431.15 | 1.1–2.0 (4m, 12H); 3.55 (m, 1H); 3.8 (m, 1H); 4.1 (d, 1H); 7.35; 7.45; 7.9; 8.70 (4d, 8H); 10.8 (s, 1H) |
| 10 | 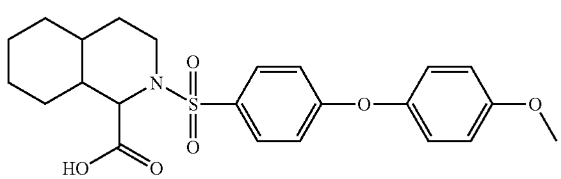 | 445.54 | 446.1 447.1 | |
| 11 | 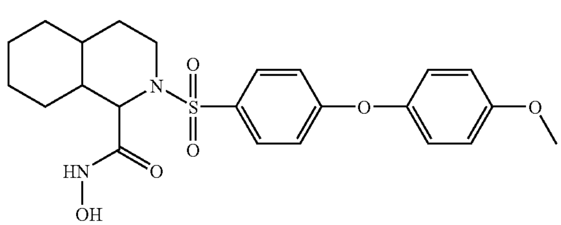 | 460.55 | 461.2 462.2 | 1.1–1.95 (4m, 12H); 3.45 (m, 1H); 3.7 (m, 1H); 3.8 (s, 2H); 4.05 (d, 1H); 7.0 (m, 4H); 7.1 (m, 2H); 7.7 (m, 2H); 10.8 (s, 1H). |

TABLE 2-continued

| Example | Structure | Molecular Weight | ES+ | 1H-NMR |
|---|---|---|---|---|
| 12 | 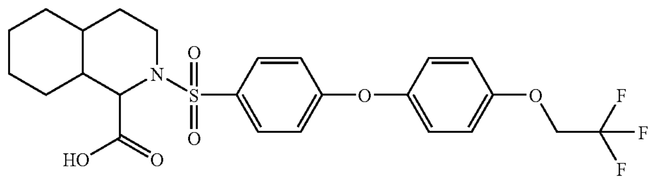 | 513.54 | 514.15 515.2 | |
| 13 | 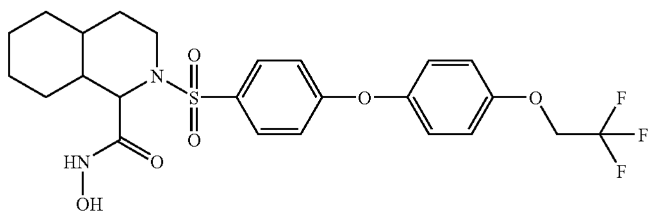 | 528.55 | 529.2 530.2 | 1.1–2.0 (4m, 12H); 3.45 (m, 1H); 3.7 (m, 1H); 4.07 (d, 1H); 7.0 (d, 2H); 7.17 (s, 4H); 7.7 (d, 2H); 10.8 (s, 1H). |
| 14 | CHIRAL | 448.9726 | 449.15.4 51.10 | 1.1–2.0 (4m, 12H); 3.5–3.8 (2m, 2H); 4.15 (d, 1H); 7.55–7.9 (3m, 8H); 8.9 (s, 1H); 10.9 (s, 1H) |
| 15 | CHIRAL | 448.9726 | 449.15.4 51.10 | 1.1–2.0 (4m, 12H); 3.5–3.8 (2m, 2H); 4.15 (d, 1H); 7.55–7.9 (3m, 8H); 8.9 (s, 1H); 10.9 (s, 1H) |
| 16 | 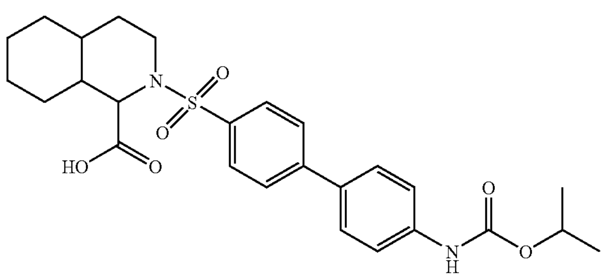 | 500.6187 | 501.18 | 1.25 (d, 6H); 1.2–1.7 (m, 11H); 2.05 (m, 1H); 3.44; 4.20; 4.90 (3m, 3–4H); 7.6; 7.7 (dd, 4H); 7.87 (m, 4H); 9.8 (s, 1H); 12.8 (s, 1H) |
| 17 | 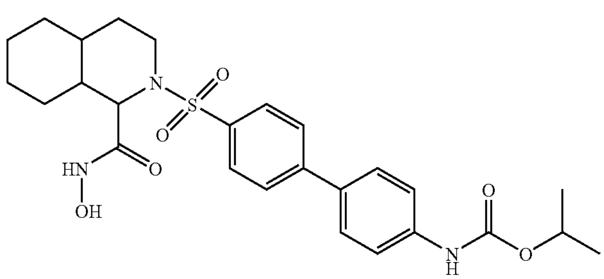 | 515.6334 | 516.19 | 1.25 (d, 6H); 1.1–1.95 (m, 12H); 3.55; 3.75; 4.12; 4.91 (4m, 4H); 7.6–7.88 (2dd, 8H) |

TABLE 2-continued

| Example | Structure | Molecular Weight | ES+ | 1H-NMR |
|---|---|---|---|---|
| 18 | 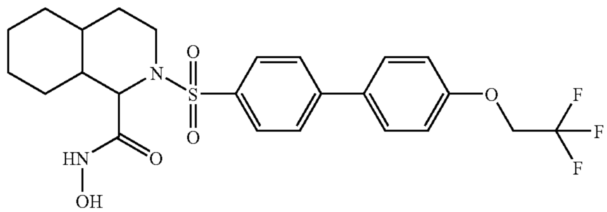 | 512.5524 | 513.13 | 1.1–2.0 (m, 12H); 3.50; 3.75, 4.11; 4.83 (4m, 5H); 7.2 (d, 2H); 7.8 (m, 6H); 8.9 (s, 1H); 10.9 (s, 1H). |
| 19 | 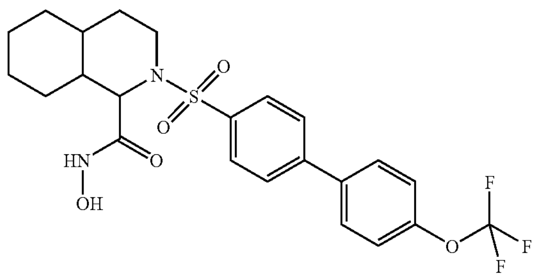 | 498.5253 | 450.08 | 1.1–2.0 (m, 12H); 3.50; 3.75, 4.15 (3m, 3H); 7.5 (d, 2H); 7.9 (m, 6H); 8.9 (s, 1H); 10.9 (s, 1H). |
| 20 | 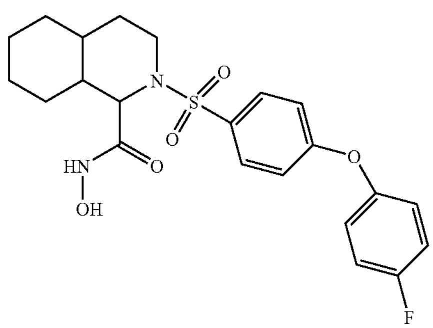 | 448.5174 | 449.24 | 1.1–2.0 (m, 12H); 3.50; 3.75, 4.10 (3m, 3H); 7.0–7.7 (4m, 8H); 8.9 (s, 1H); 10.9 (s, 1H). |
| 21 | CHIRAL | 448.5174 | 449.21 | 1.1–2.0 (m, 12H); 3.50; 3.75, 4.10 (3m, 3H); 7.0–7.7 (4m, 8H); 8.9 (s 1H); 10.9 (s, 1H) |
| 22 | 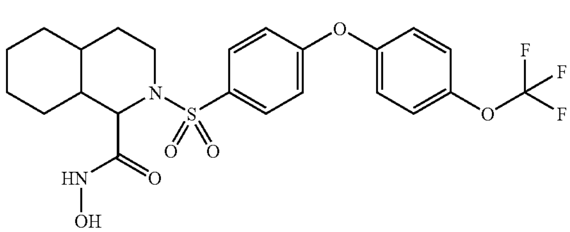 | 499.51 | 500.18 | 1.2–1.7 (m, 11H); 2.05 (m, 1H); 3.5 (m, +/− 2H); 4.2 (d, 1H); 7.15–7.80 (4m ("d"), 8H); 12.7 (s, 1H) |
| 23 | 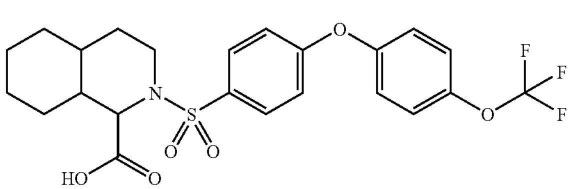 | 514.5247 | 515.21 | 1.1–2.0 (m, 12H); 3.50; 3.75, 4.10 (3m, 3H); 7.1–7.8 (4m ("d"), 8H); 8.9 (s, 1H); 10.9 (s, 1H) |

TABLE 2-continued

| Example | Structure | Molecular Weight | ES+ | 1H-NMR |
|---|---|---|---|---|
| 24 | 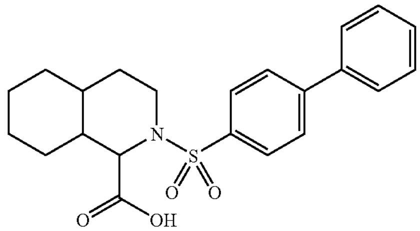 | 399.5129 | 400.24 | 1.1–2.0 (4m, 12H); 3.5–3.8 (2m, 2H); 4.15 (d, 1H); 7.4–8.0 (m, 9H) |
| 25 | 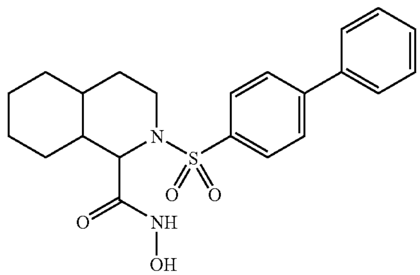 | 414.5275 | 415.26 | 1.1–2.0 (4m, 12H); 3.5–3.8 (2m, 2H); 4.15 (d, 1H); 7.4–8.0 (m, 9H); 8.9 (s, 1H); 10.9 (s, 1H) |
| 26 | 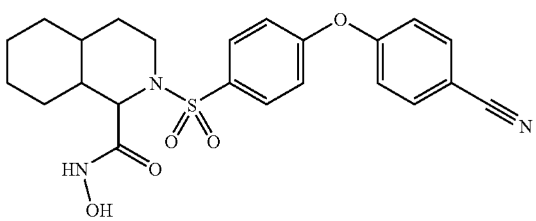 | 455.5368 | 456.30 | 1.1–2.0 (m, 12H); 3.50; 3.75, 4.10 (3m, 3H); 7.2 (m, 4H); 7.8–8.0 (dd, 4H); 8.9 (s, 1H); 10.9 (s, 1H) |
| 27 | 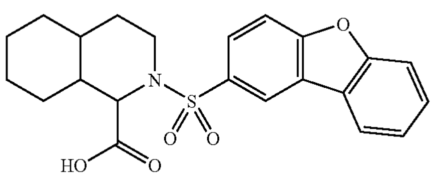 | 413.4963 | 414.14 | 1.2–1.7 (m, 11H); 2.05 (m, 1H); 3.5 (m, +/− 2H); 4.3 (d, 1H); 7.5–7.9 (6m, 7H); 8.7 (s, 1H) |
| 28 | 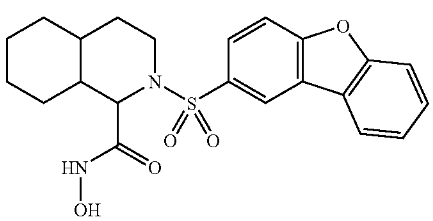 | 428.511 | 429.21 | 1.1–2.0 (m, 12H); 3.60; 3.75, 4.10 (3m, 3H); 7.5–8.9 (7m, 8H); 10.9 (s, 1H) |
| 29 | 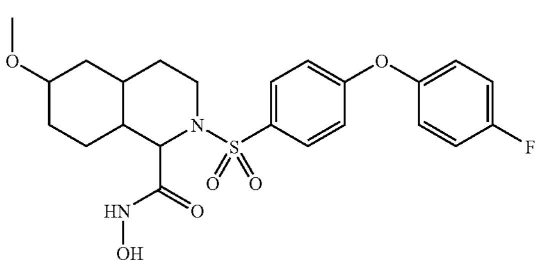 | 478.5438 | 479.22 | 1.0–1.95 (m) and 2.6–4.05 (m, together 14H); 3.7 (s, H); 6.7–7.8 (8m, 8H); 8.9 (s, 1H); 10.9 (2s, 1H) |

Experimental

Pharmacological Examples a) Determining the enzyme activity of the catalytic domain of human collagenase-1 (MMP-1).

This protein is obtained as an inactive proenzyme from Biocol, Potsdam (catalog No. MMP1). Activation of the proenzyme:

2 parts by volume of proenzyme are incubated, at 37° C. for 1 hour, with 1 part by volume of APMA solution. The APMA solution is prepared from a 10 mmol/l solution of p-aminophenylmercuric acetate in 0.1 mmol/l NaOH by diluting with 3 parts by volume of tris/HCl buffer, pH 7.5 (see below). The pH is adjusted to between 7.0 and 7.5 by adding 1 mmol/l HCl. After the enzyme has been activated, it is diluted with the tris/HCl buffer to a concentration of 2.5 µg/ml.

In order to measure the enzyme activity, 10 µl of enzyme solution are incubated for 15 minutes with 10 µl of a 3% (v/v) buffered solution of dimethyl sulfoxide (reaction 1). In order to measure the enzyme inhibitor activity, 10 µl of enzyme solution are incubated with 10 µl of a 3% (v/v) buffered solution of dimethyl sulfoxide which contains the enzyme inhibitor (reaction 2).

Both in the case of reaction 1 and in the case of reaction 2, the enzyme reaction is monitored by fluorescence spectroscopy (328 nm (extinction)/393 nm (emission)) after adding 10 µl of a 3% (v/v) aqueous solution of dimethyl sulfoxide which contains 0.3 mmol of the substrate/l.

The enzyme activity is presented as increase in extinction/minute.

The inhibitory effect is calculated as percentage inhibition using the following formula:

% inhibition=100−[(increase in extinction/minute in reaction 2)/(increase in extinction/minute in reaction 1)×100].

The $IC_{50}$, i.e. the inhibitor concentration which is required for 50% inhibition of the enzyme activity, is determined graphically by plotting the percentage inhibitions at different inhibitor concentrations. The buffer solution contains 0.05% Brij (Sigma, Deisenhofen, Germany) and also 0.1 mol of tris/HCl/l, 0.1 mol of NaCl/l, 0.01 mol of $CaCl_2$/l (pH=7.5).

The enzyme solution contains 2.5 µg of the enzyme domain/ml.

The substrate solution contains 0.3 mmol of the fluorogenic substrate (7-methoxycoumarin-4-yl)acetyl-Pro-Leu-Gly-Leu-3-(2',4'-dinitrophenyl)-L-2,3-diaminopropionyl-Ala-Arg-$NH_2$/l (Bachem, Heidelberg, Germany).

b) Preparation, and determination of the enzyme activity, of the catalytic domain of human stromelysin (MMP-3) and neutrophilic collagenase (MMP-8).

The two enzymes, i.e. stromelysin (MMP-3) and neutrophilic collagenase (MMP-8), were prepared as described by Ye et al. (Biochemistry; 31 (1992) pages 11231–11235). In order to measure the enzyme activity or the inhibitory effect on the enzyme, 10 µl of enzyme solution were incubated, for 15 minutes, with 10 µl of a 3% (v/v) buffered solution of dimethyl sulfoxide which contained the enzyme inhibitor, where appropriate. After 10 µl of a 3% (v/v) aqueous solution of dimethyl sulfoxide which contained 1 mmol of substrate/l had been added, the enzyme reaction was monitored by fluorescence spectroscopy (328 nm (ex)/393 nm(em)).

The enzyme activity is presented as increase in extinction/minute. The $IC_{50}$ values listed in Table 2 were determined as the inhibitor concentrations which in each case resulted in the enzyme being inhibited by 50%.

The buffer solution contained 0.05% Brij (Sigma, Deisenhofen, Germany) as well as 0.1 mol of tris/HCl/l, 0.1 mol of NaCl/l, 0.01 mol of $CaCl_2$/l and 0.1 mol of piperazine-N,N'-bis[2-ethanesulfonic acid]/l (pH=7.5). The MMP-3 enzyme solution contained 2.3 µg, and the MMP-8 enzyme solution contained 0.6 µg, of one of the enzyme domains/ml prepared as described by Ye et al. The substrate solution contained 1 mmol of the fluorogenic substrate (7-methoxycoumarin-4-yl)acetyl-Pro-Leu-Gly-Leu-3-(2',4'-dinitrophenyl)-L-2,3-diaminopropionyl-Ala-Arg-$NH_2$/l (Bachem, Heidelberg, Germany).

c) Determining the enzyme activity of the catalytic domain of human collagenase-3 (MMP-13).

This protein was obtained as an inactive proenzyme from INVITEK, Berlin (catalog No. 30 100 803). Activation of the proenzyme:

2 parts by volume of proenzyme were incubated, at 37° C. for 1.5 hours, with 1 part by volume of APMA solution. The APMA solution was prepared from a 10 mmol/l solution of p-aminophenylmercuric acetate in 0.1 mmol/l NaOH by diluting the solution with 3 parts by volume of tris/HCl buffer, pH 7.5 (see below). The pH was adjusted to between 7.0 and 7.5 by adding 1 mmol/l HCl. After the enzyme had been activated, it was diluted with the tris/HCl buffer to a concentration of 1.67 µg/ml.

In order to measure the enzyme activity, 10 µl of enzyme solution were incubated for 15 minutes with 10 µl of a 3% (v/v) buffered solution of dimethyl sulfoxide (reaction 1). In order to measure the enzyme inhibitor activity, 10 µl of enzyme solution were incubated with 10 µl of a 3% (v/v) buffered solution of dimethyl sulfoxide which contained the enzyme inhibitor (reaction 2).

Both in the case of reaction 1 and in the case of reaction 2, the enzyme reaction was monitored by fluorescence spectroscopy (328 nm (extinction)/393 nm (emission)) after 10 µl of a 3% (v/v) aqueous solution of dimethyl sulfoxide which contained 0.075 mmol of the substrate/l had been added.

The enzyme activity was presented as increase in extinction/minute.

The effect of the inhibitor was calculated as a percentage inhibition in accordance with the following formula: % inhibition=100−[(increase in extinction/minute in reaction 2)/(increase in extinction/minute in reaction 1)×100].

The $IC_{50}$, that is the concentration of inhibitor which is required for 50% inhibition of the enzyme activity, was determined graphically by plotting the percentage inhibitions at different inhibitor concentrations.

The buffer solution contained 0.05% Brij (Sigma, Deisenhofen, Germany) and also 0.1 mol of tris/HCl/l, 0.1 mol of NaCl/l, 0.01 mol of $CaCl_2$/l (pH=7.5). The enzyme solution contained 1.67 µg of the enzyme domain/ml. The substrate solution contained 0.075 mmol of the fluorogenic substrate (7-methoxycoumarin-4-yl)acetyl-Pro-Leu-Gly-Leu-3-(2',4'-dinitrophenyl)-L-2,3-diaminopropionyl-Ala-Arg-$NH_2$/l (Bachem, Heidelberg, Germany).

d) Determining the enzyme activity of the catalytic domain of human gelatinase A (MMP-2). This protein was obtained as an inactive proenzyme from INVITEK, Berlin (catalog No. 30 100 602). Activation of the proenzyme:

2 parts by volume of proenzyme were incubated, at 37° C. for 0.5 hour, with 1 part by volume of APMA solution. The APMA solution was prepared from a 10 mmol/l solution of p-aminophenylmercuric acetate in 0.1 mmol/l NaOH by diluting it with 3 parts by volume of tris/HCl buffer, pH 7.5

(see below). The pH was adjusted to between 7.0 and 7.5 by adding 1 mmol/l HCl. After the enzyme had been activated, it was diluted with the tris/HCl buffer to a concentration of 0.83 µg/ml.

In order to measure the enzyme activity, 10 µl of enzyme solution were incubated for 15 minutes with 10 µl of a 3% (v/v) buffered solution of dimethyl sulfoxide (reaction 1). In order to measure the enzyme inhibitor activity, 10 µl of enzyme solution were incubated with 10 µl of a 3% (v/v) buffered solution of dimethyl sulfoxide which contained the enzyme inhibitor (reaction 2).

Both in the case of reaction 1 and in the case of reaction 2, the enzyme reaction was monitored by fluorescence spectroscopy (328 nm (extinction)/393 nm (emission)) after 10 µl of a 3% (v/v) aqueous solution of dimethyl sulfoxide which contained 0.3 mmol of the substrate/l had been added.

The enzyme activity was presented as increase in extinction/minute.

The effect of the inhibitor was calculated as percentage inhibition in accordance with the following formula: % inhibition=100−[(increase in extinction/minute in reaction 2)/(increase in extinction/minute in reaction 1)×100].

The $IC_{50}$, that is the concentration of inhibitor which is required for 50% inhibition of the enzyme activity, was determined graphically by plotting the percentage inhibitions at different inhibitor concentrations.

The buffer solution contained 0.05% Brij (Sigma, Deisenhofen, Germany) and also 0.1 mol of tris/HCl/l, 0.1 mol of NaCl/l, 0.01 mol of $CaCl_2$/l (pH=7.5). The enzyme solution contained 0.83 µg of the enzyme domain/ml. The substrate solution contained 0.3 mmol of the fluorogenic substrate (7-methoxycoumarin-4-yl)acetyl-Pro-Leu-Gly-Leu-3-(2',4'-dinitrophenyl)-L-2,3-diaminopropionyl-Ala-Arg-$NH_2$/l (Bachem, Heidelberg, Germany).

e) Determining the enzyme activity of the catalytic domain of human gelatinase B (MMP-9). This protein was obtained as an inactive proenzyme from Roche, Mannheim (catalog No. 1 758 896). Activation of the proenzyme:

2 parts by volume of proenzyme were incubated, at 37° C. for 4 hours, with 1 part by volume of APMA solution. The APMA solution was prepared from a 10 mmol/l solution of p-aminophenylmercuric acetate in 0.1 mmol/l NaOH by diluting it with 3 parts by volume of tris/HCl buffer, pH 7.5 (see below). The pH was adjusted to between 7.0 and 7.5 by adding 1 mmol/l HCl. After the enzyme had been activated, it was diluted with the tris/HCl buffer to a concentration of 4.2 mU/ml.

In order to measure the activity of the enzyme, 10 µl of enzyme solution were incubated for 15 minutes with 10 µl of a 3% (v/v) buffered solution of dimethyl sulfoxide (reaction 1). In order to measure the enzyme inhibitor activity, 10 µl of enzyme solution were incubated with 10 µl of a 3% (v/v) buffered solution of dimethyl sulfoxide which contained the enzyme inhibitor (reaction 2). Both in the case of reaction 1 and in the case of reaction 2, the enzyme reaction was monitored by fluorescence spectroscopy (328 nm (extinction)/393 nm (emission)) after 10 ul of a 3% (v/v) aqueous solution of dimethyl sulfoxide, which contained 0.15 mmol of the substrate/l, had been added.

The enzyme activity was presented as increase in extinction/minute.

The inhibitory effect was calculated as percentage inhibition in accordance with the following formula: % inhibition=100−[(increase in extinction/minute in reaction 2)/(increase in extinction/minute in reaction 1)×100].

The $IC_{50}$, that is the concentration of inhibitor which is required for 50% inhibition of the enzyme activity, was determined graphically by plotting the percentage inhibitions at different inhibitor concentrations.

The buffer solution contained 0.05% Brij (Sigma, Deisenhofen, Germany) and also 0.1 mol of tris/HCl/l, 0.1 mol of NaCl/l, 0.01 mol of $CaCl_2$/l (pH=7.5). The enzyme solution contained 4.2 mU of the enzyme domain/ml. The substrate solution contained 0.15 mmol of the fluorogenic substrate (7-methoxycoumarin-4-yl)acetyl-Pro-Leu-Gly-Leu-3-(2',4'-dinitrophenyl)-L-2,3-diaminopropionyl-Ala-Arg-$NH_2$/ (Bachem, Heidelberg, Germany).

Table 3 below shows the results.

TABLE 3

| Example | MMP-1 $IC_{50}$ [nM] | MMP-2 $IC_{50}$ [nM] | MMP-3 $IC_{50}$ [nM] | MMP-8 $IC_{50}$ [nM] | MMP-9 $IC_{50}$ [nM] | MMP-13 $IC_{50}$ [nM] |
|---|---|---|---|---|---|---|
| 3 | 400 | 30 | 40 | 3 | 100 | 3 |
| 5 | 70 | 2 | 28 | 2.5 | 1.2 | 1.8 |
| 7 | 600 | 4 | 65 | 13 | 3 | 7 |
| 9 | 1000 | 20 | 160 | 22 | 12 | 21 |
| 11 | 220 | 2 | 25 | 2.5 | 2 | 1.5 |
| 13 | 180 | 2.6 | 30 | 4 | 2 | 2 |
| 14 | 400 | 2 | 25 | 2.2 | 3.5 | 2 |
| 15 | 6000 | 2300 | 10000 | 2000 | 4000 | 2300 |
| 19 | 2100 | 3 | 59 | 10 | 5 | 3 |
| 20 | 41 | 2 | 26 | 3 | 2 | 2 |
| 21 | 21 | 1.5 | 23 | 2.3 | 0.45 | 1.3 |
| 23 | 290 | 2 | 50 | 9 | 2 | 2.1 |
| 26 | 450 | 8 | 41 | 16 | 3 | 3 |

What is claime is:
1. A compound of the formula I

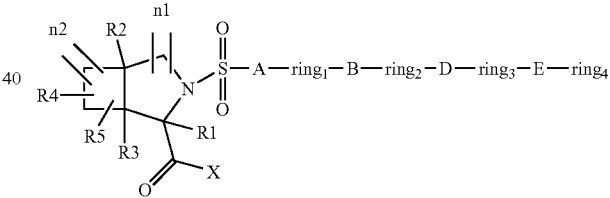

wherein,
A is —($C_0$–$C_4$)-alkylene;
B, D and E are, independently of each other, are —($C_0$–$C_4$)-alkylene or the radical —B1-B2-B3-wherein,
B1 is —$(CH_2)_n$—, in which n is the integer zero, 1 or 2,
B3 is —$(CH_2)_m$—, in which m is the integer zero, 1 or 2,
with the proviso that the sum of n and m amounts to zero, 1 or 2, and
B2 is
1) —C(O)—
2) —($C_2$–$C_4$)-alkenylene,
3) —$S(O)_o$—, wherein o is the integer zero, 1 or 2,
4) —N(R6)-, wherein R6 is hydrogen, methyl or ethyl,
5) —N(R6)-C(Y)—, wherein Y is oxygen or sulfur,
6) —C(Y)—N(R6)-, wherein Y is oxygen or sulfur,
7) —N(R6)-$SO_2$—,
8) —$SO_2$—N(R6)-,
9) —N(R6)-$SO_2$—N(R6)-, 10) —N(R6)-C(Y)—N(R6)-, wherein Y is oxygen or sulfur,
11) —O—C(O)—N(R6)-,
12) —NH—C(O)—O—,
13) —O—,
14) —C(O)—O—,
15) —O—C(O)—,
16) —O—C(O)—O—,
17) —O—CH$_2$—C(O)—,
18) —O—CH$_2$—C(O)—O—,
19) —O—CH$_2$—C(O)—N(R6)-,
20) —C(O)—CH$_2$—O—,
21) —O—C(O)—CH$_2$—O—,
22) —N(R6)-C(O)—CH$_2$—O—,
23) —O—(CH$_2$)$_n$—O—, wherein n is the integer 2 or 3, or
24) —O—(CH$_2$)$_m$—N(R6)-, wherein m is the integer 2 or 3,
25) —N(R6)-(CH$_2$)$_m$—O—, wherein m is the integer 2 or 3,
26) —N(R6)-N(R6)-,
27) —N=N—,
28) —N(R6)-CH=N—,
29) —N=CH—N(R6)-,
30) —N(R6)-C(R7)=N—, wherein R7 is —NH—R6,
31) —N=C(R7)-N(R6)-, wherein R7 is —NH—R6, or
32) —(C$_2$–C$_6$)-alkynylene;

ring 1, ring 2 and ring 3, independently of each other, are
1) a covalent bond,
2) —(C$_6$–C$_{14}$)-aryl, that is unsubstituted or substituted, independently of each other, one, two or three times by G, as defined below,
3) 4- to 5-membered Het ring, that is unsubstituted or substituted, independently of each other, one, two or three times by G, or
4) 6-membered Het ring, that contains 1 heteroatom selected from the group consisting of N, O and S, and that is unsubstituted or substituted, independently of each other, one, two or three times by G;

ring 4 is
1) —(C$_6$–C$_{14}$)-aryl, that is unsubstituted or substituted, independently of each other, one, two or three times by G,
2) 4- to 5-membered Het ring, that is unsubstituted or substituted, independently of each other, one, two or three times by G,
3) 6-membered Het ring, that contains 1 heteroatom selected from the group consisting of N, O and S, and that is unsubstituted or substituted, independently of each other, one, two or three times by G; or
4)

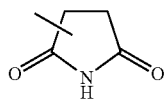 or 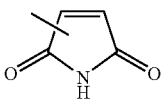

that is unsubstituted or substituted once by G;

G is
1) hydrogen,
2) halogen,
3) =O,
4) —(C$_1$–C$_6$)-alkyl, that is unsubstituted or substituted, one, two or three times, by halogen, —(C$_3$–C$_6$)-cycloalkyl, —(C$_2$–C$_6$)-alkynyl, —(C$_6$–C$_{14}$)-aryl or a Het ring,
5) —(C$_6$–C$_{14}$)-aryl,
6) a Het ring,
7) —C(O)—O—R10, wherein R10 is
  a) —(C$_1$–C$_6$)-alkyl, that is unsubstituted or substituted, one or two times by —(C$_3$–C$_6$)-cycloalkyl, —(C$_2$–C$_6$)-alkynyl, —(C$_6$–C$_{14}$)-aryl or a Het ring, or
  b) —(C$_6$–C$_{14}$)-aryl, or
  c) a Het ring,
8) —C(S)—O—R10,
9) —C(O)—NH—R11, wherein R11 is
  a) —(C$_1$–C$_6$)-alkyl, that is unsubstituted or substituted, one or two times by —(C$_3$–C$_6$)-cycloalkyl, —(C$_2$–C$_6$)-alkynyl, —(C$_6$–C$_{14}$)-aryl or a Het ring, or
  b) —(C$_6$–C$_{14}$)-aryl, or
  c) a Het ring,
10) —C(S)—NH—R11,
11) —O—R12, wherein R12 is
  a) hydrogen,
  b) —(C$_1$–C$_6$)-alkyl, that is unsubstituted or substituted, one, two or three times, by halogen, —(C$_3$–C$_6$)-cycloalkyl, —(C$_2$–C$_6$)-alkynyl, —(C$_6$–C$_{14}$)-aryl or a Het ring,
  c) —(C$_6$–C$_{14}$)-aryl,
  d) a Het ring,
  e) —C(O)—O—R13, wherein, R13 is
    i) —(C$_1$–C$_6$)-alkyl, that is unsubstituted or substituted, one or two times by —(C$_3$–C$_6$)-cycloalkyl, —(C$_2$–C$_6$)-alkynyl, —(C$_6$–C$_{14}$)-aryl, or a Het ring, or
    ii) —(C$_6$–C$_{14}$)-aryl, or
    iii) a Het ring,
  f) —C(S)—O—R13,
  g) —C(O)—NH—R14, wherein R14 is
    i) —(C$_1$–C$_6$)-alkyl, that is unsubstituted or substituted, one or two times by —(C$_3$–C$_6$)-cycloalkyl, —(C$_2$–C$_6$)-alkynyl, —(C$_6$–C$_{14}$)-aryl or a Het ring, or
    ii) —(C$_6$–C$_{14}$)-aryl, or
    iii) a Het ring, or
  h) —C(S)—NH—R14,
12) —C(O)—R10,
13) —S(O)$_p$—R12, wherein p is the integer zero, 1 or 2,
14) —NO$_2$,
15) —CN, or
16) —N(R15)-R12, wherein R15 is
  i) hydrogen,
  ii) —(C$_1$–C$_6$)-alkyl, or
  iii) —SO$_2$—(C$_1$–C$_6$)-alkyl, wherein the alkyl is unsubstituted or substituted, one or two times by —(C$_3$–C$_6$)-cycloalkyl, —(C$_2$–C$_6$)-alkynyl, —(C$_6$–C$_{14}$)-aryl or a Het ring, or
17) —SO$_2$—N(R12)-R1, wherein, R1 is defined as below;
X is —OH or —NH—OH;
n1 is 2;
n2 is 3;
and
R1, R2, R3, R4 and R5 are identical or different and are, independently of each other,
1) hydrogen, 2) —(C$_1$–C$_6$)-alkyl, that is unsubstituted or substituted, one or two times by —(C$_3$–C$_6$)-cycloalkyl, —(C$_2$–C$_6$)-alkynyl, —(C$_6$–C$_{14}$)-aryl or a Het ring,
3) —C(O)—O—R8, wherein R8 is
  i) hydrogen,
  ii) —(C$_1$–C$_6$)-alkyl, that is unsubstituted or substituted, one or two times by —(C$_3$–C$_6$)-cycloalkyl, —(C$_2$–C$_6$)-alkynyl, —(C$_6$–C$_{14}$)-aryl or a Het ring, or substituted one, two, three, four or fives times, by fluorine, or
  iii) —(C$_6$–C$_{14}$)-aryl or a Het ring,
4) —O—R8, or
5) —(C$_3$–C$_6$)-cycloalkyl; or a stereoisomer or a mixture of stereoisomer thereof in any ratio, or a physiologically tolerable salt thereof.

2. The compound according to claim 1 wherein,
A is —(C$_0$–C$_4$)-alkylene;
ring 1, ring 2 and ring 3, are identical or different and are, independently of each other,
1) —(C$_6$–C$_{14}$)-aryl selected from the group consisting of phenyl and naphthyl, that is unsubstituted or substituted, independently of each other, one, two or three times, by G, or
2) 4- to 6-membered Het ring selected from the group consisting of azetidinyl, dihydrofuranyl, dioxolyl, furanyl, furazanyl, imidazolidinyl, imidazolinyl, imidazolyl, isothiazolidinyl, 2-isothiazolinyl, isothiazolyl, isoxazolyl, isoxazolidinyl, 2-isoxazolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxothiolanyl, piperidinyl, pyranyl, pyroazolidinyl, pyrazolinyl, pyrazolyl, pyridinyl, pyridyl, pyrrolidinyl, pyrrolinyl, 2H-pyrrolyl, pyrrolyl, tetrahydrofuranyl, tetrahydropyridinyl, 1,2,3-thiadiazolyl, 1,2,4-thiadiazolyl, 1,2,5-thiadiazolyl, 1,3,4-thiadiazolyl, thiazolyl, thienyl, and thiophenyl, that is unsubstituted or substituted, independently of each other, one, two or three times, by G;

ring 4 is
1) —(C$_6$–C$_{14}$)-aryl selected from the group consisting of phenyl, naphthyl, 1-naphthyl, 2-naphthyl, anthryl and fluorenyl, that is unsubstituted or substituted, independently of each other, one, two or three times, by G,
2) 4- to 6-membered Het ring selected from the group consisting of azetidinyl, dihydrofuranyl, dioxolyl, furanyl, furazanyl, imidazolidinyl, imidazolinyl, imidazolyl, isothiazolidinyl, 2-isothiazolinyl, isothiazolyl, isoxazolyl, isoxazolidinyl, 2-isoxazolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxothiolanyl, piperidinyl, pyranyl, pyroazolidinyl, pyrazolinyl, pyrazolyl, pyridinyl, pyridyl, pyrrolidinyl, pyrrolinyl, 2H-pyrrolyl, pyrrolyl, tetrahydrofuranyl, tetrahydropyridinyl, 1,2,3-thiadiazolyl, 1,2,4-thiadiazolyl, 1,2,5-thiadiazolyl, 1,3,4-thiadiazolyl, thiazolyl, thienyl, and thiophenyl, that is unsubstituted or substituted, independently of each other, one, two or three times, by G, or
3)

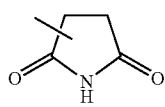 or 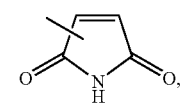, that is unsubstituted or substituted once by G;
G is
1) —C(O)—NH—R11, wherein R11 is
  a) —(C$_1$–C$_6$)-alkyl, that is unsubstituted or substituted, once or twice, by —(C$_3$–C$_6$)-cycloalkyl, —(C$_2$–C$_6$)-alkynyl, —(C$_6$–C$_{14}$)-aryl or a Het ring,
  b) —(C$_6$–C$_{14}$)-aryl, or
  c) a Het ring,
2) —O—R12, wherein R12 is
  a) hydrogen,
  b) —(C$_1$–C$_6$)-alkyl, that is unsubstituted or substituted, one, two or three times, by halogen, —(C$_3$–C$_6$)-cycloalkyl, —(C$_2$–C$_6$)-alkynyl, —(C$_6$-C$_{,4}$)-aryl or a Het ring,
  c) —(C$_6$–C$_{14}$)-aryl,
  d) a Het ring,
  e) —C(O)—O—R13, wherein R13 is
    i) —(C$_1$–C$_6$)-alkyl, that is unsubstituted or substituted, one or two times, by —(C$_3$–C$_6$)-cycloalkyl, —(C$_2$–C$_6$)-alkynyl, —(C$_6$–C$_{14}$)-aryl, or a Het ring, or
    ii) —(C$_6$–C$_{14}$)-aryl, or
    iii) a Het ring.

3. The compound according to claim 1, wherein,
B, D and E are identical or different and are, independently of each other, —(C$_0$–C$_4$)-alkylene or the radical —B1-B2-B3- wherein,
B1 is —(CH$_2$)$_n$—, wherein n is the integer zero, 1 or 2,
B3 is —(CH$_2$)$_m$—, wherein m is the integer zero, 1 or 2,
  with the proviso that the sum of n and m amounts to zero, 1 or 2, and
B2 is
  1) —C(O)—
  2) ethenylene,
  3) —S—,
  4) —N(R6)-C(O)—, wherein R6 is hydrogen, methyl or ethyl,
  5) —C(O)—N(R6)-,
  6) —O—, or
  7) ethynylene;

ring 1, ring 2 and ring 3 are identical or different and are, independently of each other,
1) —(C$_6$–C$_{14}$)-aryl selected from the group consisting of phenyl and naphthyl, that is unsubstituted or substituted, independently of each other, one or two times, by G, or
2) 4- to 6-membered Het ring selected from the group consisting of dihydrofuranyl, furanyl, pyridinyl, pyrrolyl, thiadiazolyl, thiazolyl and thiophenyl, that is unsubstituted or substituted, independently of each other, one or two times, by G;

ring 4 is
1) —(C$_6$–C$_{14}$)-aryl selected from the group consisting of phenyl and naphthyl, that is unsubstituted or substituted, independently of each other, one or two times, by G,
2) 4- to 6-membered Het ring selected from the group consisting of dihydrofuranyl, furanyl, piperidinyl, pyridinyl, pyrrolyl, pyrrolidinyl, thiazolyl and thiophenyl, that is unsubstituted or substituted, independently of each other, one or two times, by G, or

3)

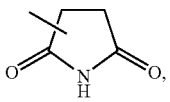

that is unsubstituted or substituted once by G;
G is 1) hydrogen,
  2) Br, Cl or F,
  3) —($C_1$–$C_4$)-alkyl, that is unsubstituted or substituted one or two times by F, phenyl, —$C_3$-cycloalkyl or a Het ring,
  4) phenyl,
  5) a Het ring,
  6) —C(O)—O—R10, wherein R10 is
    a) —($C_1$–$C_6$)-alkyl, that is unsubstituted or substituted, one or two times, by cyclopropyl, phenyl or a Het ring,
    b) phenyl, or
    c) a Het ring,
  7) —C(O)—NH—R11, wherein R11 is
    a) —($C_1$–$C_6$)-alkyl, that is unsubstituted or substituted, one or two times, by cyclopropyl, phenyl or a Het ring,
    b) phenyl, or
    c) a Het ring,
  8) —O—R12, wherein R12 is
    a) hydrogen,
    b) —($C_1$–$C_6$)-alkyl, that is unsubstituted or substituted, one, two or three times by halogen, cyclopropyl, phenyl or a Het ring,
    c) phenyl,
    d) a Het ring,
    e) —C(O)—O—R13, wherein R13 is
      i) —($C_1$–$C_6$)-alkyl, that is unsubstituted or substituted, one or two times, by cyclopropyl, phenyl or a Het ring, or
      ii) phenyl, or
      iii) a Het ring,
    f) —C(S)—O—R13, or
    g) —C(O)—NH—R14, wherein R14 is
      i) —($C_1$–$C_6$)-alkyl, that is unsubstituted or substituted, one or two times, by phenyl or a Het ring, or
      ii) phenyl or
      a Het ring,
  9) —C(O)—R10,
  10) —S(O)$_p$—R12, wherein p is the integer 1 or 2,
  11) —$NO_2$,
  12) —CN, or
  13) —N(R15)-R12, wherein R15 is
    i) hydrogen, or
    ii) ($C_1$–$C_6$)-alkyl;
R1, R2 and R3 are hydrogen; and
R4 and R5 are identical or different and are, independently of each other,
  1) hydrogen,
  2) methyl or ethyl, or
  3) —OH.

4. The compound according to claim 1, wherein,
B, D and E are identical or different and are, independently of each other, —($C_0$–$C_4$)-alkylene or the radical —B1-B2-B3- wherein,
B1 is —($CH_2$)$_n$—, wherein n is the integer zero, 1 or 2,
B3 is —($CH2$)$_m$—, wherein m is the integer zero, 1 or 2,
  with the proviso that the sum of n and m amounts to zero, 1 or 2, and
B2 is
  1) ethenylene, or
  2) ethynylene;
ring 1, ring 2 and ring 3 are identical or different and are, independently of each other,
  2) phenyl, that is unsubstituted or substituted, independently of each other, one or two times, by G, or
  3) 4- to 6-membered Het ring selected from consisting of dihydrofuranyl, furanyl, piperidinyl, pyridinyl, pyrrolyl, thiazolyl and thiophenyl, that is unsubstituted or substituted, independently of each other, one or two times, by G;
ring 4 is
1) phenyl, that is unsubstituted or substituted, independently of each other, one or two times, by G,
2) 4- to 6-membered Het ring selected from the group consisting of dihydrofuranyl, furanyl, piperidinyl, pyridinyl, pyrimidinyl, pyridothiophenyl, pyrrolyl, pyrrolidinyl, thiazolyl and thiophenyl, that is unsubstituted or substituted, independently of each other, one or two times, by G, or
3)

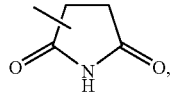

that is unsubstituted or substituted once by G;
G is
  1) hydrogen,
  2) Br, Cl or F,
  3) —($C_1$–$C_4$)-alkyl, that is unsubstituted or substituted one, two or three times, by
    Br, Cl, F, —$C_3$-Cycloalkyl, phenyl or a Het ring,
  4) phenyl,
  5) a Het ring,
  6) —C(O)—O—R10, wherein R10 is
    a) —($C_1$–$C_6$)-alkyl, that is unsubstituted or substituted, one or two times, by cyclopropyl, phenyl or a Het ring,
    b) phenyl, or
    c) a Het ring,
  7) —C(O)—NH—R11, wherein R11 is
    a) —($C_1$–$C_6$)-alkyl, that is unsubstituted or substituted, one or two times, by cyclopropyl, phenyl or a Het ring,
    b) phenyl or naphthyl, or
    c) a Het ring,
  8) —O—R12, wherein R12 is
    a) hydrogen,
    b) —($C_1$–$C_6$)-alkyl, that is unsubstituted or substituted, one, two or three times, by halogen, cyclopropyl, phenyl or a Het ring,
    c) phenyl,
    d) a Het ring,
    e) —C(O)—O—R13, wherein R13 is
      e)1) —($C_1$–$C_6$)-alkyl, that is unsubstituted or substituted, one or two times, by cyclopropyl, phenyl, naphthyl, or a Het ring, or
      e)2) phenyl, or
      e)3) a Het ring, f) —C(S)—O—R13, or
g) —C(O)—NH—R14, wherein R14 is
  i) —(C$_1$–C$_6$)-alkyl, that is unsubstituted or substituted, one or two times, by phenyl or a Het ring, or
  ii) phenyl, or
  iii) a Het ring,
9) —C(O)—R10,
10) —S(O)$_p$—R12, wherein p is an integer 1 or 2,
11) —NO$_2$,
12) —CN, or
13) —N(R15)-R12, wherein R15 is
  i) hydrogen, or
  ii) —(C$_1$–C$_6$)-alkyl;
X is —OH or —NH—OH;
and
R1, R2, R3, R4 and R5 are hydrogen.

5. The compound according to claim 1, wherein,
A is a covalent bond or —CH$_2$—CH$_2$—;
B, D and E are identical or different and are, independently of each other, —(C$_0$–C$_4$)-alkylene or the radical —B1-B2-B3- wherein,
  B1 is —(CH$_2$)$_n$—, wherein n is the integer zero, 1 or 2,
  B3 is —(CH2)$_m$—, wherein m is the integer zero, 1 or 2,
  with the proviso that the sum of n and m amounts to zero, 1 or 2, and
  B2 is
  1) —C(O)—
  2) —(C$_2$–C$_4$)-alkynylene,
  3) —S(O)$_o$—, wherein o is the integer zero or 1,
  4) —N(R6)-C(Y)—, wherein Y is oxygen and R6 is hydrogen,
  5) —C(Y)—N(R6)-, wherein Y is oxygen and R6 is hydrogen, or
  6) —O—;
ring 1, ring 2 and ring 3 are identical or different and are, independently of each other,
  1) phenyl, that is unsubstituted or substituted, independently of each other, one or two times, by G, or
  2) 4- to 6-membered Het ring selected from consisting of furanyl, pyridinyl, and thiophenyl, that is unsubstituted or substituted, independently of each other, one or two times, by G; or
ring 4 is
1) phenyl, that is unsubstituted or substituted, independently of each other, one or two times, by G,
2) 4- to 6-membered Het ring selected from the group consisting of furanyl, piperidinyl, pyridinyl, pyrrolyl, pyrrolidinyl, thiazolyl and thiophenyl, that is unsubstituted or substituted, independently of each other, one or two times, by G, or
3)

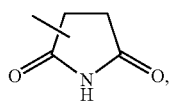

that is unsubstituted or substituted once by G;
G is 1) hydrogen,
  2) Br, Cl or F,
  3) —(C$_1$–C$_4$)-alkyl, that is unsubstituted or substituted one, two or three times, by Br, Cl, F, —C$_3$-cycloalkyl, phenyl or a Het ring,
  4) phenyl,
  5) a Het ring,
  6) —C(O)—O—R10, wherein R10 is
    a) —(C$_1$–C$_6$)-alkyl, that is unsubstituted or substituted, one or two times, by cyclopropyl, phenyl or a Het ring,
    b) phenyl, or
    c) a Het ring,
  7) —C(O)—NH—R11, wherein R11 is
    a) —(C$_1$–C$_6$)-alkyl, that is unsubstituted or substituted, one or two times, by cyclopropyl, phenyl or a Het ring,
    b) phenyl, or
    c) a Het ring,
  11) —O—R12, wherein R12 is
    a) hydrogen,
    b) —(C$_1$–C$_6$)-alkyl, that is unsubstituted or substituted, one, two or three times, by halogen, cyclopropyl, phenyl or a Het ring,
    c) phenyl,
    d) a Het ring,
    e) —C(O)—O—R13, wherein R13 is
      i) —(C$_1$–C$_6$)-alkyl, that is unsubstituted or substituted, one or two times, by cyclopropyl, phenyl or a Het ring, or
      ii) phenyl, or
      iii) a Het ring,
    f) —C(S)—O—R13,
    g) —C(O)—NH—R14, wherein R14 is
      i) —(C$_1$–C$_6$)-alkyl, that is unsubstituted or substituted, one or two times, by phenyl or a Het ring, or
      ii) phenyl, or
      iii) a Het ring,
  9) —C(O)—R10,
  10) —S(O)$_p$—R12, wherein p is the integer zero, 1 or 2,
  11) —NO$_2$,
  12) —CN, or
  13) —N(R15)-R12, wherein R15 is
    i) hydrogen, or
    ii) —(C$_1$–C$_6$)-alkyl;
X is —NH—OH;
and
R1, R2, R3, R4 and R5 are hydrogen.

6. The compound according to claim 1, which is:
2-(4'-nitrobiphenyl-4-sulfonyl)decahydroisoquinoline-1-(N-hydroxy)carboxamide;
2-(4'-chlorobiphenyl-4-sulfonyl)decahydroisoquinoline-1-carboxylic acid;
2-(4'-chlorobiphenyl-4-sulfonyl)decahydroisoquinoline-1-(N-hydroxy)carboxamide;
2-(6-phenoxypyridine-3-sulfonyl)decahydroisoquinoline-1-carboxylic acid trifluoroacetate;
2-(6-phenoxypyridine-3-sulfonyl)decahydroisoquinoline-1-(N-hydroxy)carboxamide trifluoroacetate;
2-[2-(4'-chlorobiphenyl-4-yl)ethanesulfonyl]decahydroisoquinoline-1-carboxylic acid;
2-[2-(4'-chlorobiphenyl-4-yl)ethanesulfonyl]decahydroisoquinoline-1-(N-hydroxy)carboxamide;
2-[4-(pyridin-4-yloxy)benzenesulfonyl]decahydroisoquinoline-1-carboxylic acid trifluoroacetate;
2-[4-(pyridin-4-yloxy)benzenesulfonyl]decahydroisoquinoline-1-(N-hydroxy)carboxamide trifluoroacetate;
2-[4-(4-methoxyphenoxy)benzenesulfonyl]decahydroisoquinoline-1-carboxylic acid;

2-[4-(4-methoxyphenoxy)benzenesulfonyl]decahydroiso-
quinoline-1-(N-hydroxy)carboxamide;
2-{4-[4-(2,2,2-trifluoroethoxy)phenoxy]
benzenesulfonyl}decahydroisoquinoline-1-carboxylic
acid;
2-{4-[4-(2,2,2-trifluoroethoxy)phenoxy]
benzenesulfonyl}decahydroisoquinoline-1-(N-hy-
droxy)carboxamide;
2-[4'-(2,2,2-trifluoroethoxy)biphenyl-4-sulfonyl]decahy-
droisoquinoline-1-carboxylic acid;
2-(4'-isopropoxycarbonylaminobiphenyl-4-sulfonyl)
decahydroisoquinoline-1-carboxylic acid;
[4'-(1-hydroxycarbamoyloctahydroisoquinoline-2-sulfo-
nyl)biphenyl-4-yl]carboxamide isopropyl ester;
2-[4'-(2,2,2-trifluoroethoxy)biphenyl-4-sulfonyl]decahy-
droisoquinoline-1-(N-hydroxy)carboxamide;
2-(4'-trifluoromethoxybiphenyl-4-sulfonyl)decahydroiso-
quinoline-1-(N-hydroxy)carboxamide;
2-[4-(4-fluorophenoxy)benzenesulfonyl]decahydroiso-
quinoline-1-(N-hydroxy)carboxamide;
2-[4-(4-trifluoromethoxyphenoxy)benzenesulfonyl]
decahydroisoquinoline-1-(N-hydroxy)carboxamide;
2-[4-(4-trifluoromethoxyphenoxy)benzenesulfonyl]
decahydroisoquinoline-1-carboxylic acid; 2-(biphenyl-
4-sulfonyl)decahydroisoquinoline-1-(N-hydroxy)car-
boxamide;
2-(biphenyl-4-sulfonyl)decahydroisoquinoline-1-car-
boxylic acid;
2-[4-(4-cyanophenoxy)benzenesulfonyl]decahydroiso-
quinoline-1-(N-hydroxy)carboxamide;
2-(dibenzofuran-2-sulfonyl)decahydroisoquinoline-1-
carboxylic acid;
2-(dibenzofuran-2-sulfonyl)decahydroisoquinoline-1-(N-
hydroxy)carboxamide; or
2-[4-(4-fluorophenoxy)benzenesulfonyl]-6-methoxy-
decahydroisoquinoline-1-(N-hydroxy)carboxamide.

7. A process for the preparation of a compound according to claim 1, comprising,
a) reacting a compound of formula IV,

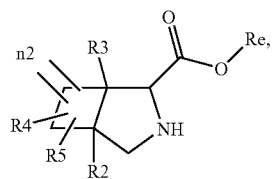

wherein, Re is hydrogen, or an ester-protecting group, with a compound of formula (V),

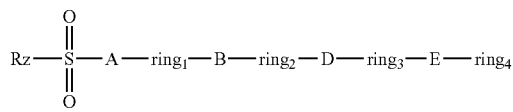

wherein, Rz is chlorine, imidazoyl or OH,
in the presence of a base, or following silylation with a suitable silylating agent, or using a suitable dehydrating agent, when Rz=OH, to give a compound of the formula (VI),

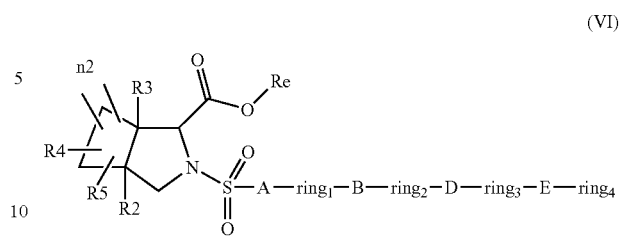

wherein, Re is an ester-protecting group, and
b) reacting a compound of the formula (VI), prepared as described in a), with a solution of alkali such as NaOH or LiOH, and then treating the product with acid, to give the carboxylic acid according to formula (I), wherein, X=OH, corresponding to a compound of formula (VII), with modifications to one of rings1, ring2, ring3 or ring4, also previously made, where appropriate, or
converting the ester-protecting group, by treating it with a mineral acid, such as hydrochloric acid, to yield a free carboxylic acid of the formula (VII),

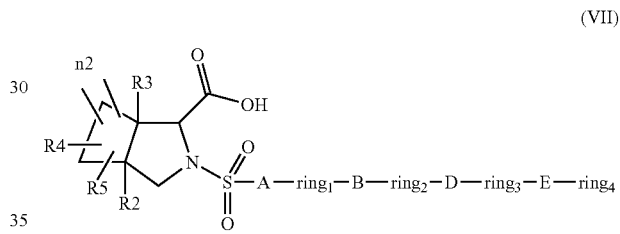

and then, converting a compound of formula (VII) into the hydroxamic acid, wherein, X=NH—OH, of formula (I), or
c) separating the compound of formula (I), prepared as described in a), or a suitable precursor to formula (I), to give enantiomerically pure compounds of formula (I), by,
i) forming a salt using enantiomerically pure acids or bases,
ii) performing chromatography using chiral stationary phases, or
iii) derivatizing the compound of formula (I) using chiral, enantiomerically pure compounds, such as amino acids, and then, separating resulting diastereomers, and eliminating chiral auxiliary groups, or
d) isolating the compound of the formula (I), prepared as described in procedures b) or c),
i) in free form, or,
ii) when acid or basic groups are present, converting the compound of formula (I) into physiologically tolerated salts.

8. A pharmaceutical preparation according to claim 1, comprising a pharmaceutically effective amount of at least one compound of formula (I), in all its stereoisomeric forms and mixtures thereof, in any ratio, or its physiologically tolerated salt, and a pharmaceutically acceptable carrier.

* * * * *